United States Patent
Kawanabe et al.

(10) Patent No.: US 10,473,801 B2
(45) Date of Patent: Nov. 12, 2019

(54) RADIATION IMAGING APPARATUS, RADIATION IMAGING SYSTEM, METHOD OF CONTROLLING RADIATION IMAGING APPARATUS, AND NON-TRANSITORY COMPUTER-READABLE STORAGE MEDIUM

(71) Applicant: CANON KABUSHIKI KAISHA, Tokyo (JP)

(72) Inventors: Jun Kawanabe, Kawasaki (JP); Minoru Watanabe, Yokohama (JP); Keigo Yokoyama, Kawasaki (JP); Sho Sato, Tokyo (JP); Kentaro Fujiyoshi, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 5 days.

(21) Appl. No.: 15/969,842

(22) Filed: May 3, 2018

(65) Prior Publication Data

US 2018/0321397 A1 Nov. 8, 2018

(30) Foreign Application Priority Data

May 8, 2017 (JP) ................................ 2017-092566

(51) Int. Cl.
*G01T 1/24* (2006.01)
*G01T 1/02* (2006.01)
(Continued)

(52) U.S. Cl.
CPC ............... *G01T 1/247* (2013.01); *A61B 6/42* (2013.01); *A61B 6/54* (2013.01); *G01T 1/023* (2013.01);
(Continued)

(58) Field of Classification Search
CPC combination set(s) only.
See application file for complete search history.

(56) References Cited

U.S. PATENT DOCUMENTS 7,205,547 B2   4/2007   Ishii et al.
7,381,963 B2   6/2008   Endo et al.
(Continued)

FOREIGN PATENT DOCUMENTS

JP   2016-040880 A1   3/2016

OTHER PUBLICATIONS

U.S. Appl. No. 15/751,600, Yoshiaki Ishii, filed Feb. 9, 2018.

*Primary Examiner* — Marcus H Taningco
*Assistant Examiner* — Djura Malevic
(74) *Attorney, Agent, or Firm* — Venable LLP

(57) ABSTRACT

A radiation imaging apparatus including conversion elements acquiring a radiation image and detectors, a readout unit and a controller is provided. In a first operation, the controller causes the readout unit to output a composition signal obtained by composing signals from the detectors, detects irradiation with radiation based on the composition signal, and shifts to a second operation. In the second operation, the controller acquires first signals individually read out from the detectors, decides a signal component, of the composition signal, which is output from a selected detector of the detectors in accordance with a ratio of the first signal from the selected detector to a sum of the first signals, and acquires an integrated dose of radiation incident on the selected detector based on the signal component and the first signal of the selected detector.

14 Claims, 14 Drawing Sheets

(51) Int. Cl.
*A61B 6/00* (2006.01)
*H04N 5/32* (2006.01)
*H04N 5/369* (2011.01)
*H04N 5/378* (2011.01)

(52) U.S. Cl.
CPC .............. *G01T 1/026* (2013.01); *H04N 5/32* (2013.01); *H04N 5/3696* (2013.01); *H04N 5/378* (2013.01); *A61B 6/4233* (2013.01); *A61B 6/542* (2013.01)

(56) References Cited

U.S. PATENT DOCUMENTS

| | | | |
|---|---|---|---|
| 7,381,965 B2 | 6/2008 | Ishii et al. | |
| 7,386,089 B2 | 6/2008 | Endo et al. | |
| 7,408,167 B2 * | 8/2008 | Kameshima | H01L 27/14663 250/370.09 |
| 7,421,063 B2 | 9/2008 | Takenaka et al. | |
| 7,435,968 B2 * | 10/2008 | Watanabe | H01L 27/14609 250/370.09 |
| 7,465,933 B2 | 12/2008 | Ishii et al. | |
| 7,514,663 B2 | 4/2009 | Yagi et al. | |
| 7,541,591 B2 | 6/2009 | Endo et al. | |
| 7,541,617 B2 | 6/2009 | Mochizuki et al. | |
| 7,573,038 B2 | 8/2009 | Yokoyama et al. | |
| 7,573,041 B2 | 8/2009 | Kameshima et al. | |
| 7,613,277 B2 | 11/2009 | Takenaka et al. | |
| 7,629,564 B2 | 12/2009 | Mochizuki et al. | |
| 7,642,517 B2 | 1/2010 | Ishii et al. | |
| 7,645,976 B2 | 1/2010 | Watanabe et al. | |
| 7,718,973 B2 | 5/2010 | Endo et al. | |
| 7,724,874 B2 | 5/2010 | Kameshima et al. | |
| 7,732,776 B2 | 6/2010 | Takenaka et al. | |
| 7,750,309 B2 | 7/2010 | Endo et al. | |
| 7,750,422 B2 | 7/2010 | Watanabe et al. | |
| 7,791,035 B2 | 9/2010 | Yokoyama et al. | |
| 7,812,313 B2 | 10/2010 | Mochizuki et al. | |
| 7,812,317 B2 | 10/2010 | Watanabe et al. | |
| 7,847,263 B2 | 12/2010 | Yagi et al. | |
| 7,850,367 B2 | 12/2010 | Takenaka et al. | |
| 7,858,947 B2 | 12/2010 | Mochizuki et al. | |
| 7,869,568 B2 | 1/2011 | Yokoyama et al. | |
| 7,880,145 B2 | 2/2011 | Yagi et al. | |
| 7,923,695 B2 | 4/2011 | Ishii et al. | |
| 7,932,946 B2 | 4/2011 | Ishii et al. | |
| 7,965,817 B2 | 6/2011 | Kameshima et al. | |
| 8,067,743 B2 | 11/2011 | Ishii et al. | |
| 8,084,745 B2 | 12/2011 | Mochizuki et al. | |
| 8,093,562 B2 | 1/2012 | Yokoyama et al. | |
| 8,107,588 B2 | 1/2012 | Kameshima et al. | |
| 8,154,641 B2 | 4/2012 | Nomura et al. | |
| 8,222,611 B2 | 7/2012 | Yagi et al. | |
| 8,247,779 B2 * | 8/2012 | Kameshima | A61B 6/4233 250/370.09 |
| 8,368,027 B2 | 2/2013 | Ishii et al. | |
| 8,680,472 B2 | 3/2014 | Mochizuki et al. | |
| 8,723,996 B2 | 5/2014 | Yokoyama et al. | |
| 8,792,024 B2 | 7/2014 | Takenaka et al. | |
| 8,809,795 B2 | 8/2014 | Takenaka et al. | |
| 8,829,438 B2 | 9/2014 | Sato et al. | |
| 8,878,972 B2 | 11/2014 | Wayama et al. | |
| 9,048,154 B2 | 6/2015 | Takenaka et al. | |
| 9,128,196 B2 | 9/2015 | Sato et al. | |
| 9,134,432 B2 | 9/2015 | Iwashita et al. | |
| 9,234,966 B2 | 1/2016 | Sugawara et al. | |
| 9,270,903 B2 | 2/2016 | Wayama et al. | |
| 9,277,896 B2 | 3/2016 | Ofuji et al. | |
| 9,423,512 B2 | 8/2016 | Sato et al. | |
| 9,423,513 B2 * | 8/2016 | Watanabe | H04N 5/32 |
| 9,462,989 B2 | 10/2016 | Takenaka et al. | |
| 9,468,414 B2 | 10/2016 | Ryu et al. | |
| 9,470,800 B2 | 10/2016 | Iwashita et al. | |
| 9,521,347 B2 | 12/2016 | Kawanabe et al. | |
| 9,541,653 B2 * | 1/2017 | Iwashita | H04N 5/32 |
| 9,625,585 B1 | 4/2017 | Yokoyama et al. | |
| 9,661,240 B2 | 5/2017 | Fujiyoshi et al. | |
| 9,675,307 B2 | 6/2017 | Ofuji et al. | |
| 9,726,767 B2 | 8/2017 | Kawanabe et al. | |
| 9,812,474 B2 | 11/2017 | Yagi et al. | |
| 9,835,732 B2 | 12/2017 | Fujiyoshi et al. | |
| 9,838,638 B2 | 12/2017 | Furumoto et al. | |
| 9,848,845 B2 * | 12/2017 | Tajima | H04N 5/32 |
| 9,948,871 B2 | 4/2018 | Wayama et al. | |
| 9,977,135 B2 | 5/2018 | Yokoyama et al. | |
| 2006/0065845 A1 * | 3/2006 | Yamaguchi | G01T 1/2928 250/370.09 |
| 2010/0148080 A1 | 6/2010 | Endo et al. | |
| 2010/0294942 A1 * | 11/2010 | Mochizuki | H01L 27/14609 250/366 |
| 2011/0317054 A1 | 12/2011 | Kameshima et al. | |
| 2012/0001079 A1 * | 1/2012 | Okada | H04N 5/32 250/366 |
| 2012/0049077 A1 * | 3/2012 | Okada | H01L 27/14603 250/370.08 |
| 2012/0199751 A1 * | 8/2012 | Watanabe | H04N 5/32 250/370.09 |
| 2013/0342514 A1 * | 12/2013 | Yokoyama | G09G 5/003 345/204 |
| 2014/0112448 A1 | 4/2014 | Takenaka et al. | |
| 2014/0151769 A1 | 6/2014 | Wayama et al. | |
| 2014/0154833 A1 | 6/2014 | Wayama et al. | |
| 2014/0239186 A1 | 8/2014 | Sato et al. | |
| 2014/0239187 A1 * | 8/2014 | Iwashita | H04N 5/32 250/394 |
| 2014/0361189 A1 | 12/2014 | Kameshima et al. | |
| 2015/0182182 A1 * | 7/2015 | Tajima | H04N 5/32 378/189 |
| 2015/0346361 A1 * | 12/2015 | Watanabe | H04N 5/32 250/369 |
| 2016/0047920 A1 * | 2/2016 | Yokoyama | G01N 23/04 378/62 |
| 2016/0270755 A1 | 9/2016 | Takenaka et al. | |
| 2018/0006080 A1 | 1/2018 | Fujiyoshi et al. | |
| 2018/0008215 A1 | 1/2018 | Wayama et al. | |
| 2018/0055464 A1 | 3/2018 | Watanabe et al. | |
| 2018/0136343 A1 | 5/2018 | Terui et al. | |

\* cited by examiner

F I G. 2
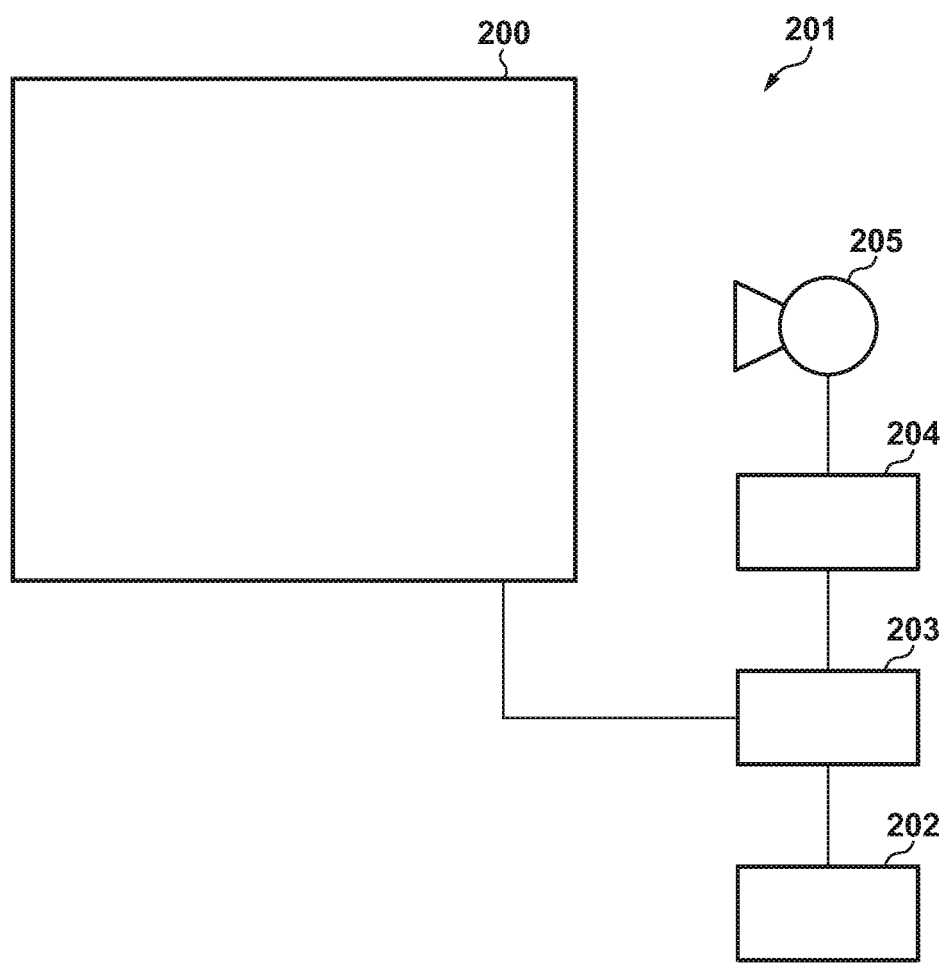

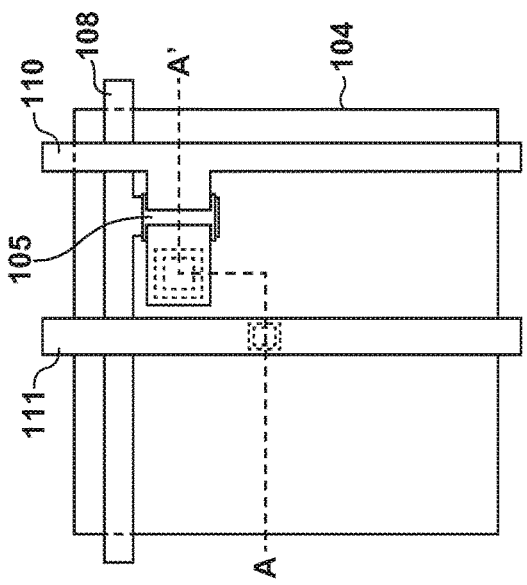
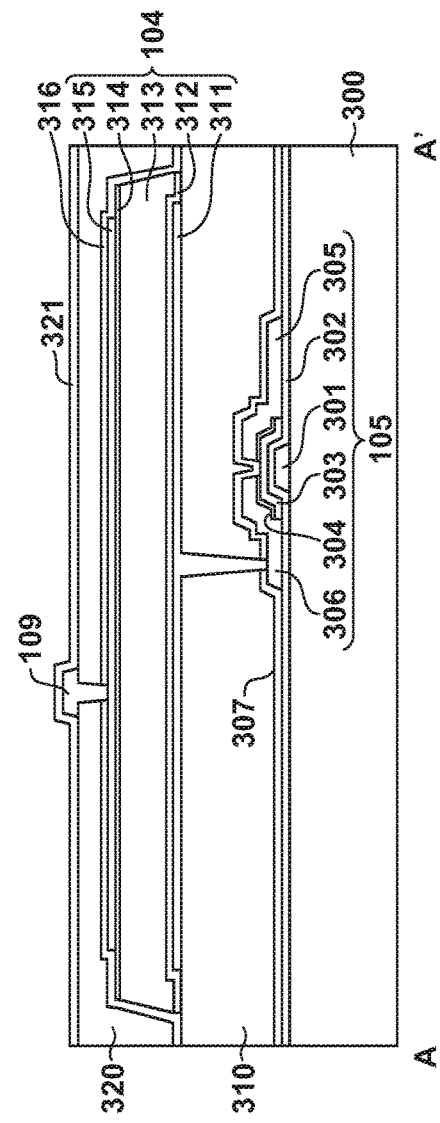
FIG. 3A
FIG. 3B

RADIATION IMAGING APPARATUS, RADIATION IMAGING SYSTEM, METHOD OF CONTROLLING RADIATION IMAGING APPARATUS, AND NON-TRANSITORY COMPUTER-READABLE STORAGE MEDIUM

BACKGROUND OF THE INVENTION

Field of the Invention

The present invention relates to a radiation imaging apparatus, a radiation imaging system, a method of controlling the radiation imaging apparatus, and a non-transitory computer-readable storage medium.

Description of the Related Art

As an imaging apparatus used for medical image diagnosis and non-destructive examination, a radiation imaging apparatus including an imaging panel having an array of pixels, each obtained by combining a conversion element for converting radiation into electric charge and a switch element such as a TFT (Thin-Film Transistor), has been widely used. Such a radiation imaging apparatus is known to monitor radiation incident on the apparatus itself. Japanese Patent Laid-Open No. 2016-40880 discloses a technique of detecting the start of irradiation with radiation and measuring the integrated dose of radiation incident on each detection element by using a signal output from the detection element for monitoring incident radiation.

SUMMARY OF THE INVENTION

Japanese Patent Laid-Open No. 2016-40880 discloses a technique of detecting the start of irradiation with radiation with high sensitivity by making a plurality of detection elements output signals to a common signal line and acquiring a composition signal. Japanese Patent Laid-Open No. 2016-40880 also discloses a technique of measuring the integrated dose of radiation incident on each detection element by making the detection element output a signal upon detection of the start of irradiation with radiation. However, Japanese Patent Laid-Open No. 2016-40880 makes no mention on handling of a composition signal acquired to detect the start of irradiation with radiation when measuring the dose of incident radiation. Assume that in measuring the integrated dose of radiation, a composition signal obtained until the detection of the start of irradiation with radiation is not used. In this case, the dose of radiation incident until the start of irradiation with radiation is detected after the actual start of irradiation with radiation is not reflected in integrated dose measurement. This may degrade the accuracy of the measurement. The influence of this degradation in accuracy can be noticeable when, for example, imaging is performed with incident radiation having high intensity in a short time of irradiation with radiation.

According to some embodiments of the present invention, there is provided a technique advantageous in measuring the integrated dose of radiation incident on a radiation imaging apparatus.

According to some embodiments, a radiation imaging apparatus comprising an image sensing region including a plurality of conversion elements configured to acquire a radiation image, a plurality of detection units arranged in the image sensing region and configured to monitor incident radiation, a readout unit configured to read out signals from the plurality of detection units, and a control unit, wherein the control unit executes a first operation and a second operation, in the first operation, the control unit causes the readout unit to output a composition signal obtained by composing signals from the plurality of detection units, detects a start of irradiation with radiation based on the composition signal, and shifts to the second operation, and in the second operation, the control unit acquires a plurality of first signals individually read out from the plurality of detection units to the readout unit, decides a signal component, of the composition signal, which is output from a selected detection unit of the plurality of detection units in accordance with a ratio of the first signal from the selected detection unit to a sum of the plurality of first signals, and acquires an integrated dose of radiation incident on the selected detection unit based on the signal component and a first signal, of the plurality of first signals, which is output from the selected detection unit, is provided.

According to some other embodiments, a control method for a radiation imaging apparatus comprising an image sensing region including a plurality of conversion elements configured to acquire a radiation image, a plurality of detection units arranged in the image sensing region and configured to monitor incident radiation, and a readout unit configured to read out signals from the plurality of detection units, the control method including a first step and a second step, the first step including causing the readout unit to output a composition signal obtained by composing signals from the plurality of detection units, detecting a start of irradiation with radiation based on the composition signal, and shifting to the second step, and the second step including acquiring a plurality of first signals individually read out from the plurality of detection units to the readout unit, deciding a signal component, of the composition signal, which is output from a selected detection unit of the plurality of detection units in accordance with a ratio of the first signal from the selected detection unit to a sum of the plurality of first signals, and acquiring an integrated dose of radiation incident on the selected detection unit based on the signal component and a first signal, of the plurality of first signals, which is output from the selected detection unit, is provided.

According to some other embodiments, a non-transitory computer-readable storage medium storing a program for causing a computer to execute a control method for a radiation imaging apparatus comprising an image sensing region including a plurality of conversion elements configured to acquire a radiation image, a plurality of detection units arranged in the image sensing region and configured to monitor incident radiation, and a readout unit configured to read out signals from the plurality of detection units, the control method including a first step and a second step, the first step including causing the readout unit to output a composition signal obtained by composing signals from the plurality of detection units, detecting a start of irradiation with radiation based on the composition signal, and shifting to the second step, and the second step including acquiring a plurality of first signals individually read out from the plurality of detection units to the readout unit, deciding a signal component, of the composition signal, which is output from a selected detection unit of the plurality of detection units in accordance with a ratio of the first signal from the selected detection unit to a sum of the plurality of first signals, and acquiring an integrated dose of radiation incident on the selected detection unit based on the signal component and a first signal, of the plurality of first signals, which is output from the selected detection unit, is provided.

Further features of the present invention will become apparent from the following description of exemplary embodiments (with reference to the attached drawings).

BRIEF DESCRIPTION OF THE DRAWINGS

FIG. 2 is a view showing an example of the arrangement of a system using the radiation imaging apparatus in FIG. 1;

FIGS. 3A and 3B are respectively a plan view and a sectional view of a pixel of the radiation imaging apparatus in FIG. 1;

DESCRIPTION OF THE EMBODIMENTS

Figure 1:
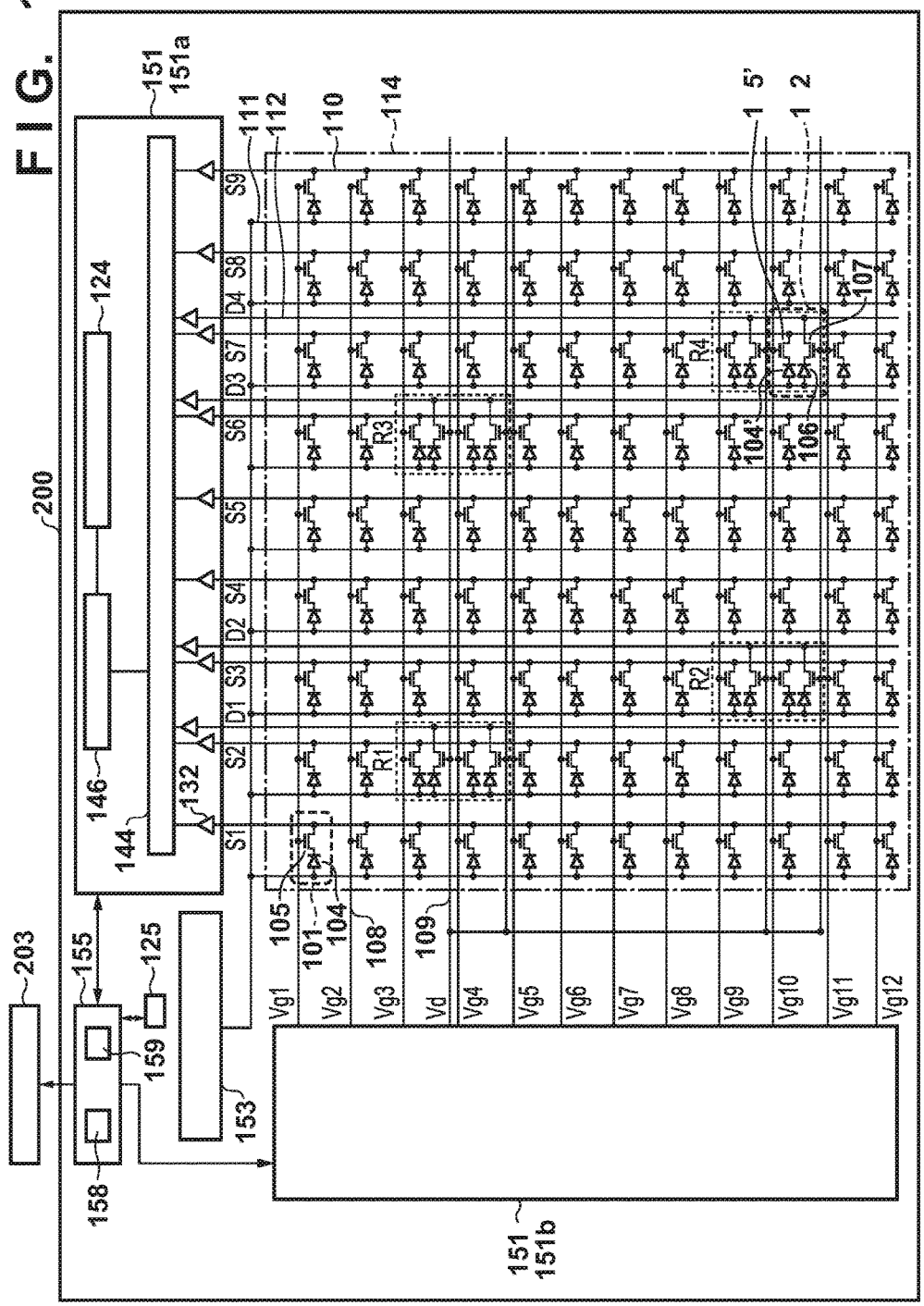
FIG. 1 is a view showing an example of the arrangement of a radiation imaging apparatus according to an embodiment of the present invention.

Concrete embodiments of a radiation imaging apparatus according to the present invention will be described with reference to the accompanying drawings. Note that in the following description and drawings, common reference numerals denote common components throughout a plurality of drawings. Accordingly, the common components will be described by cross-referencing a plurality of drawings, and a description of components denoted by common reference numerals will appropriately be omitted. Note that radiation according to the present invention can include not only α-rays, β-rays, and γ-rays that are beams generated by particles (including photons) emitted by radioactive decay but also beams having energy equal to or higher than the energy of these beams, for example, X-rays, particle rays, and cosmic rays.

The arrangement of a radiation imaging apparatus according an embodiment of the present invention will be described with reference to FIGS. 1 to 11. FIG. 1 shows an example of the arrangement of a radiation imaging apparatus 200 according to the first embodiment of the present invention. The radiation imaging apparatus 200 includes an image sensing region 114 in which a plurality of conversion elements that convert radiation into electrical signals are arranged in a two-dimensional array pattern to acquire a radiation image, a readout unit 151, a bias power supply 153, a control unit 155, and a memory unit 125. Although described in detail later, the control unit 155 can control each constituent element of the radiation imaging apparatus 200.

Pixels 101 and detection pixels 102 are arranged in the image sensing region 114. Each pixel 101 is a pixel for acquiring a radiation image, and includes a conversion element 104 that converts incident radiation into an electrical signal. Each detection pixel 102 includes a conversion element 104' for acquiring a radiation image and a conversion element 106 serving as a detection unit for monitoring incident radiation. In other words, the image sensing region 114 includes a plurality of pixels, each of which includes one conversion element 104 or 104'. Some pixels of the plurality of pixels each further include one conversion element 106 serving as a detection unit. Signals converted from radiation by the conversion elements 104 and 104' are output to a signal line 110 via switch elements 105 and 105'. A signal converted from radiation by the conversion element 106 is output to a detection signal line 112 via a switch element 107. In this embodiment, the detection pixel 102 has both a function of monitoring the incidence of radiation and a function of acquiring a radiation image. However, this is not exhaustive. For example, the detection pixel 102 may be configured to include the conversion element 106 and the switch element 107 without including the conversion element 104' and the switch element 105'. In this case, the conversion element 106 of the detection pixel 102 may have a size similar to that of the conversion element 104 of the pixel 101. The structures of the pixel 101 and the detection pixel 102 will be described later.

The arrangement shown in FIG. 1 is an example of arranging the pixels 101 and the detection pixels 102 in 12 rows×9 columns in the image sensing region 114. However, such pixels may be arranged in 1,000 rows×1,000 columns or 5,000 rows×5,000 columns. In this specification, in the structure including the plurality of pixels 101 and the plurality of detection pixels 102, the arrangement of pixels arrayed in a direction in which each signal line 110 extends is called a column direction, and the arrangement of pixels arrayed in a direction intersecting with (perpendicular to) the column direction is called a row direction.

The conversion elements 104, 104', and 106 each can be formed from a scintillator (not shown) that converts radiation into light and a photoelectric conversion element that converts light into an electrical signal. For example, the scintillator can be formed into a sheet-like shape covering the image sensing region 114 so as to be shared among the plurality of pixels 101 and the plurality of detection pixels 102. Alternatively, the conversion elements 104, 104', and 106 each can be formed from a conversion element that directly converts radiation into an electrical signal. The switch elements 105, 105', and 107 each can include, for example, a TFT (Thin-Film Transistor) whose active region is formed from a semiconductor such as amorphous silicon or polysilicon.

All the pixels 101 and all the detection pixels 102 are connected to a common bias wiring 111. The bias power supply 153 applies a predetermined bias voltage to each pixel. The switch elements 105 and 105' arranged on each row are connected to a corresponding one of control lines 108 (Vg1 to Vg12). In addition, the switch elements 107 are connected to control lines 109 (Vd) independent of the control lines 108.

The arrangement shown in FIG. 1 includes four ROIs (regions of interest) each provided with the conversion element 106 serving as a detection unit that monitors radiation. Each ROI includes the two detection pixels 102. Accordingly, the two conversion elements 106 of the two detection pixels 102 included in one ROI serve as one detection unit for monitoring incident radiation. For this reason, the term "ROI" in this specification indicates a detection unit. A specific ROI of the respective ROIs will be referred to as, for example, one of detection units R1 to R4, as shown in FIG. 1. The arrangement shown in FIG. 1 includes ROIs in 2×2 places, that is, four places. However, this is not exhaustive. For example, ROIs may be provided in 5×5 places, that is, 25 places, or 10×10 places, that is, 100 places. In addition, ROIs may be evenly arranged in the entire image sensing region 114 or may be unevenly arranged in a specific range. The arrangements of the pixels 101 and the detection pixels 102 shown in FIG. 1 each are an example and not exhaustive.

The readout unit 151 includes a processing circuit 151a and a driving circuit 151b. The readout unit 151 reads out signals from the conversion elements 104 of the pixels 101, the conversion elements 104' of the detection pixels 102, and the conversion elements 106 serving as detection units, which are arranged in the image sensing region 114, in accordance with the control unit 155.

The processing circuit 151a includes a sensing unit 132, a multiplexer 144, an analog digital (AD) converter 146, and a signal processing unit 124. The plurality of signal lines 110 and the plurality of detection signal lines 112 are connected to the corresponding sensing units 132 of the plurality of sensing units 132 arranged in the processing circuit 151a. Each sensing unit 132 includes, for example, a differential amplifier and a sample hold circuit. The multiplexer 144 selects the plurality of sensing units 132 in a predetermined order and supplies signals from the selected sensing units 132 to the AD converter 146. The AD converter 146 converts the supplied signals into digital signals and outputs them. The outputs from the AD converter 146 are supplied to the signal processing unit 124 to be processed.

The driving circuit 151b drives the switch element 105 of the pixel 101 and the switch element 105' of the detection pixel 102 via the control line 108. The driving circuit 151b also drives the switch element 107 of the detection pixel 102 via the control line 109. The driving circuit 151b is electrically connected to the control line 108 and the control line 109.

The control unit 155 controls the readout unit 151 to read out signals from the conversion elements 104, 104', and 106. The control unit 155 also controls, for example, the start and end of irradiation with radiation based on the information of signals output from the conversion elements 104, 104', and 106 which are processed by the signal processing unit 124. That is, the control unit 155 can measure the incident dose of radiation based on the dose of radiation detected by the conversion element 106 serving as a detection unit. The control unit 155 can include a CPU (Central Processing Unit) 159 that executes a program for controlling the readout unit 151 and a memory 158 storing a program for performing an imaging operation. In addition, for example, the control unit 155 may be implemented by a PLD (Programmable Logic Device) such as an FPGA (Field Programmable Gate Array). Alternatively, for example, the control unit 155 may be implemented by a general-purpose computer incorporating an ASIC (Application Specific Integrated Circuit) and programs. Furthermore, the control unit 155 may be implemented by a combination of all or some of the above constituent elements.

FIG. 2 shows an example of the arrangement of a system 201 including the radiation imaging apparatus 200. The system 201 includes, in addition to the radiation imaging apparatus 200, a controller 202, an interface 203, a radiation source interface 204, and a radiation source 205.

The user can input target dose A, an irradiation time B [ms], a tube current C [mA], a tube voltage D [kV], an ROI in which radiation is to be monitored, and the like to the controller 202. When the user operates an exposure switch attached to the controller 202 or the radiation source 205, the radiation source 205 irradiates the radiation imaging apparatus 200 with radiation through an object (not shown). When, for example, the integrated value of signals read out from the conversion elements 106 of the detection pixels 102 arranged in the ROI reaches a dose A', the control unit 155 of the radiation imaging apparatus 200 sends a signal (exposure stop signal) for stopping exposure to the radiation source interface 204. The signal for stopping exposure can be sent from the control unit 155 to the radiation source interface 204 via the interface 203. In accordance with this operation, the radiation source interface 204 causes the radiation source 205 to stop irradiation with radiation. In this case, the control unit 155 can decide the dose A' based on the target dose A, a radiation irradiation intensity, communication delays and processing delays between the respective units, and the like. When the irradiation time of radiation reaches the irradiation time B, the radiation source 205 stops irradiation with radiation regardless of the presence/absence of an exposure stop signal.

The arrangement of the pixel 101 will be described next with reference to FIGS. 3A and 3B. FIG. 3A is a plan view of the pixel 101. FIG. 3B is a sectional view taken between A-A' shown in FIG. 3A. In this embodiment, the pixel 101 includes the conversion element 104 and the switch element 105 that outputs an electrical signal corresponding to the electric charge of the conversion element 104 to the signal line 110. The conversion element 104 is stacked on an interlayer dielectric film 310 on the switch element 105 provided on an insulating substrate 300 such as a glass substrate.

The switch element 105 includes, on the substrate 300, a control electrode 301, an insulating layer 302, a semiconductor layer 303, an impurity semiconductor layer 304 higher in impurity concentration than the semiconductor layer 303, a main electrode 305, and a main electrode 306 formed sequentially from the substrate 300. Partial regions of the impurity semiconductor layer 304 are in contact with the main electrode 305 and the main electrode 306. The channel region of the switch element 105 is formed between regions, of the semiconductor layer 303, which are in contact with the partial regions of the impurity semiconductor layer 304. The control electrode 301 is electrically connected to the control line 108. The main electrode 305 is electrically connected to the signal line 110. The main electrode 306 is electrically connected to an individual electrode 311 of a conversion element. In the arrangement shown in FIG. 3B, the main electrode 305, the main electrode 306, and the signal line 110 are integrally formed from the same conductive layer, with the main electrode 305 being part of the signal line 110. An insulating layer 307 and the interlayer dielectric film 310 are arranged on the main electrode 305, the main electrode 306, and the signal line 110 sequentially from the signal line 110. This embodiment uses, as the switch element 105, an inversely-staggered type switch element using a semiconductor layer formed from amorphous silicon as a main component and an impurity semiconductor layer. However, the present invention is not limited to this. For example, it is possible to use a staggered type switch element formed from polysilicon as a main component or an organic TFT or oxide TFT as a switch element. In addition, this embodiment exemplifies the case in which an insulating substrate such as a glass substrate is used as the substrate 300. However, it is possible to use a semiconductor substrate such as a silicon substrate as the substrate 300 and a transistor formed on the substrate 300 as the switch element 105.

The interlayer dielectric film 310 is arranged between the substrate 300 and a plurality of individual electrodes 311 arranged for the respective pixels 101 so as to cover the switch element 105, and has a contact hole. The individual electrode 311 is electrically connected to the main electrode 306 through a conductive via arranged in the contact hole provided in the interlayer dielectric film 310. The conversion element 104 includes, on the interlayer dielectric film 310, the individual electrode 311, an impurity semiconductor layer 312, a semiconductor layer 313, an impurity semiconductor layer 314, and a common electrode 315 formed sequentially from the interlayer dielectric film 310. An insulating layer 316 is arranged on the common electrode 315 of the conversion element 104. The common electrode 315 of the conversion element 104 is electrically connected to the bias wiring 111 arranged on an interlayer dielectric film 320. An insulating layer 321 is arranged as a protective film on the bias wiring 111. This embodiment exemplifies the case in which a PIN photoelectric conversion element is used as the conversion element 104. However, the present invention is not limited to this. It is possible to use a MIS or TFT photoelectric conversion element. A scintillator (not shown) that converts incident radiation into light that can be photoelectrically converted by the conversion element 104 is arranged on the insulating layer 321.

Figure 4A:
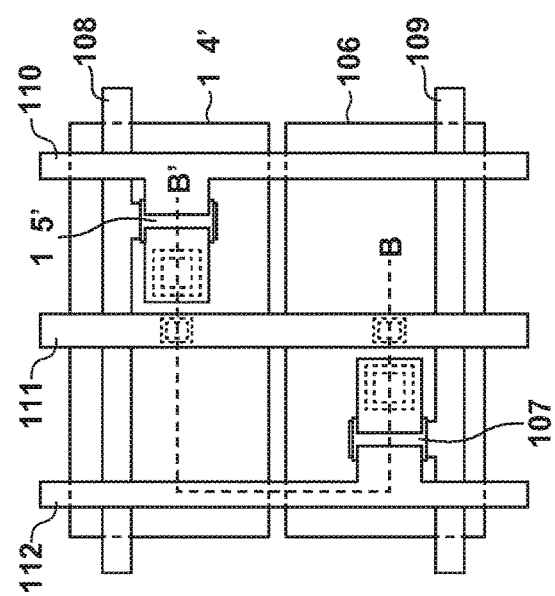
FIGS. 4A and 4B are respectively a plan view and a sectional view of a detection pixel of the radiation imaging apparatus in FIG. 1.
Figure 4B:
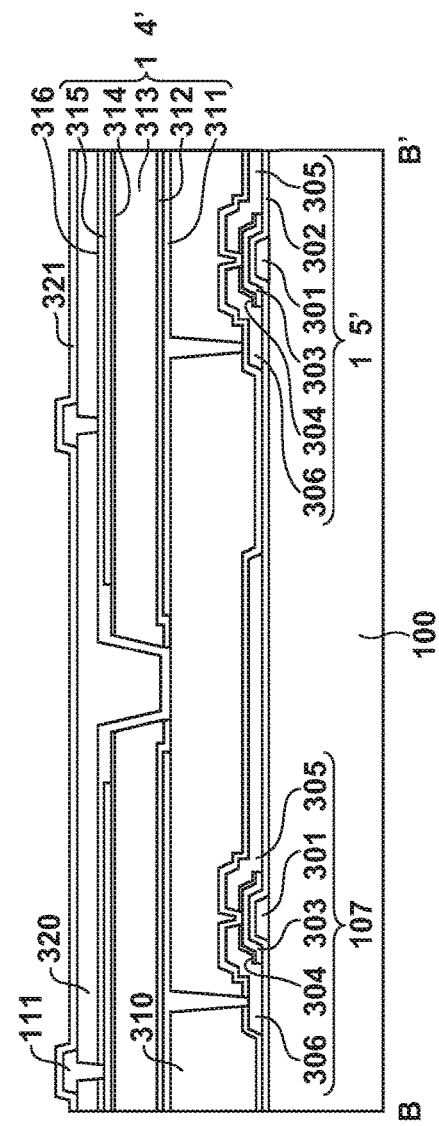

The arrangement of the detection pixel 102 will be described next with reference to FIGS. 4A and 4B. FIG. 4A is a plan view of the detection pixel 102. FIG. 4B is a sectional view taken between B-B' shown in FIG. 4A. In this embodiment, the detection pixel 102 includes the conversion element 104' for acquiring a radiation image, the switch element 105', the conversion element 106 serving as a detection unit for monitoring radiation, and the switch element 107. The conversion elements 104' and 106 each can have the same multilayer structure as that of the conversion element 104 of the pixel 101 on the interlayer dielectric film 310. The bias wiring 111 arranged on the interlayer dielectric film 320 is electrically connected to the common electrode 315 of the conversion elements 104' and 106. The individual electrode 311 of the conversion element 104' is connected to the main electrode 306 through the conductive via arranged in the contact hole provided in the interlayer dielectric film 310. The individual electrode 311 of the conversion element 106 is connected to the detection signal line 112 through the conductive via arranged in the contact hole provided in the interlayer dielectric film 310. The insulating layer 307 and the interlayer dielectric film 310 are arranged on the detection signal line 112 sequentially from the detection signal line 112.

In this embodiment, because the opening area of the conversion element 104' of the detection pixel 102 (the area of a portion that can receive light in a plan view of the image sensing region 114) is smaller than the opening area of the conversion element 104 of the pixel 101, a signal amount for the generation of a radiation image output from the detection pixel 102 decreases. However, it is possible to reduce the influence of this area difference by adjusting the gain of the sensing unit 132 or correcting a radiation image as needed. This correction can be implemented by interpolation processing using signals output from the pixels 101 arranged around the detection pixel 102.

Figure 5:
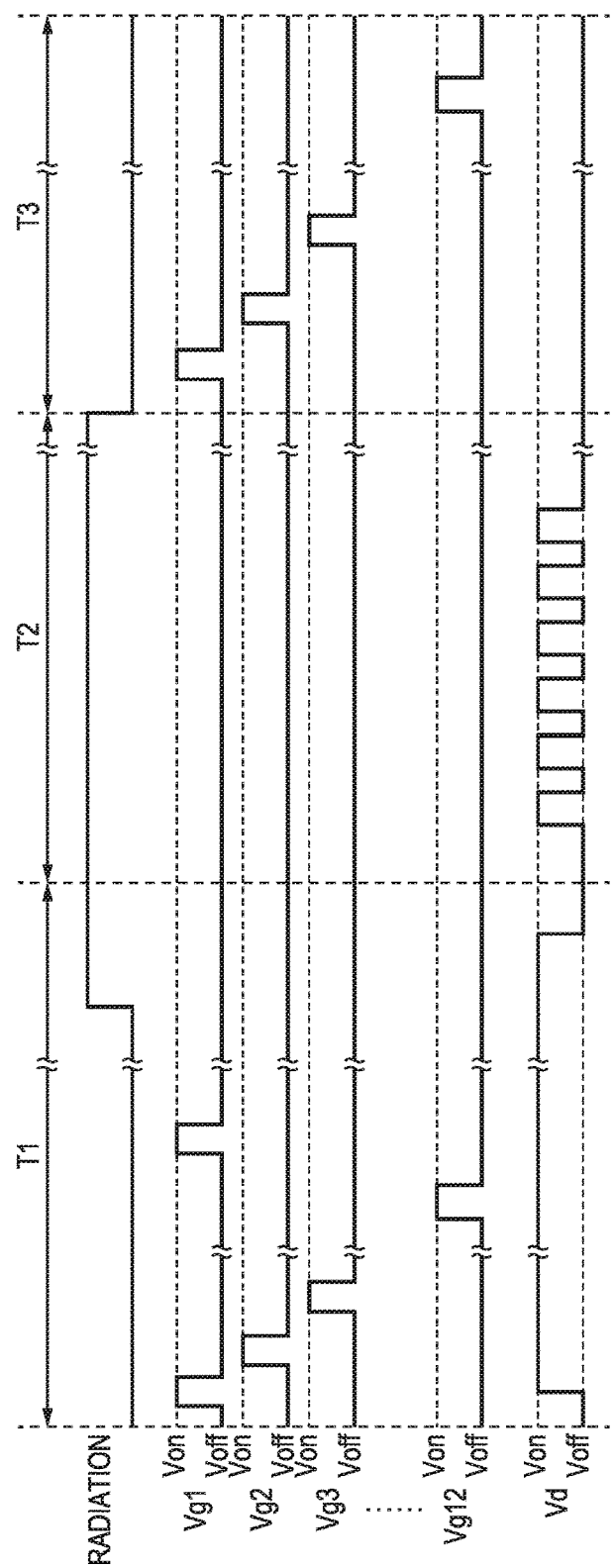
FIG. 5 is a timing chart showing the operation of the radiation imaging apparatus in FIG. 1.

The operation of the radiation imaging apparatus 200 in the first mode according to this embodiment will be described next with reference to the timing chart of FIG. 5. The first mode is a mode when any one of the detection units R1 to R4 is connected to the single detection signal line 112. Assume that in the following description, signals to be applied to the control line 108 to drive the switch element 105 of the pixel 101 and the switch element 105' of the detection pixel 102 are signals Vg1 to Vgm (m is 12 in the arrangement shown in FIG. 1). Assume also that a signal to be applied to the control line 109 to drive the switch element 107 of the detection pixel 102 is represented by a signal Vd. A voltage Von applied to the signals Vg1 to Vg12 and Vd indicates a voltage that sets the switch elements 105, 105', and 107 in the conduction state (ON state). A voltage Voff indicates a voltage that sets the switch elements 105, 105', and 107 in the nonconduction state (OFF state). A combination of the voltages of signals and conduction state of the switch elements 105, 105', and 107 can be decided by a combination of a circuit arrangement and the conductivity types of switch elements. In addition, the processing circuit 151a and the driving circuit 151b shown in FIG. 1 operate as the readout unit 151 under the control of the control unit 155, as described above.

A period T1 in FIG. 5 will be described first. In the period T1, the control unit 155 executes the operation of causing the detection units R1 to R4 to simultaneously output signals to the readout unit 151 and detecting the start of irradiation with radiation. In the period T1, the control unit 155 controls the driving circuit 151b so as to fix the signal Vd to the voltage Von, and the switch element 107 of the detection pixel 102 is fixed in the conduction state. With this operation, the control unit 155 detects the start of irradiation with radiation based on the signals output from the conversion elements 106 of the detection pixels 102 of the detection units R1 to R4 and read by the processing circuit 151a. Upon detecting the start of irradiation with radiation, the control unit 155 shifts to an operation in a period T2. In the period T1, the control unit 155 may control the driving circuit 151b to periodically reset the individual electrode 311 to a constant potential in order to remove dark currents generated in the conversion elements 104 and 104'. In the arrangement shown in FIG. 5, the control unit 155 controls the driving circuit 151b so as to sequentially apply the voltage Von to the control lines 108 (the signals Vg1 to Vg12), and the conversion elements 104 and 104' are electrically connected to the signal lines 110 (S1 to S9) fixed at the constant voltage. This prevents electric charge caused by dark currents from being accumulated in the conversion elements 104 and 104' over a long period of time. The length of the period T1 greatly varies depending on imaging techniques, conditions, and the like, and can be several sec to several min.

The period T2 in FIG. 5 will be described next. The period T2 is a period of irradiation with radiation. For example, the period T2 is the period from the instant when the start of irradiation with radiation is detected to the instant when the integrated dose of incident radiation becomes a target dose. The period T2 can be regarded as a period during which the integrated dose of incident radiation is monitored. In the period T2, the control unit 155 controls the driving circuit 151b so as to intermittently apply the voltage Von to the signal Vd, and the switch elements 107 of the detection pixels 102 are intermittently set in the conduction state. Because the control unit 155 controls the driving circuit 151b so as to always apply the voltage Voff to the signals Vg1 to Vg12, the switch elements 105 are set in the nonconduction state, and electric charge corresponding to incident radiation is accumulated in each of the conversion elements 104 and 104'. On the detection signal line 112 (for example, the detection signal line 112 (D1)), the sensing unit 132 performs a sample/hold operation, and the electric charge of the detection signal line 112 is reset at the timing when the conduction period of the switch elements 107 (for example, the detection unit R1) ends. With this control, the control unit 155 can read out signals output from the conversion elements 106 to the processing circuit 151a with high accuracy while preventing electric charge generated by parasitic capacitance. After the integrated dose of radiation read out to the processing circuit 151a reaches the target dose, the control unit 155 can control irradiation with radiation or the like by, for example, sending a signal for stopping exposure to the interface 203.

Figure 6:
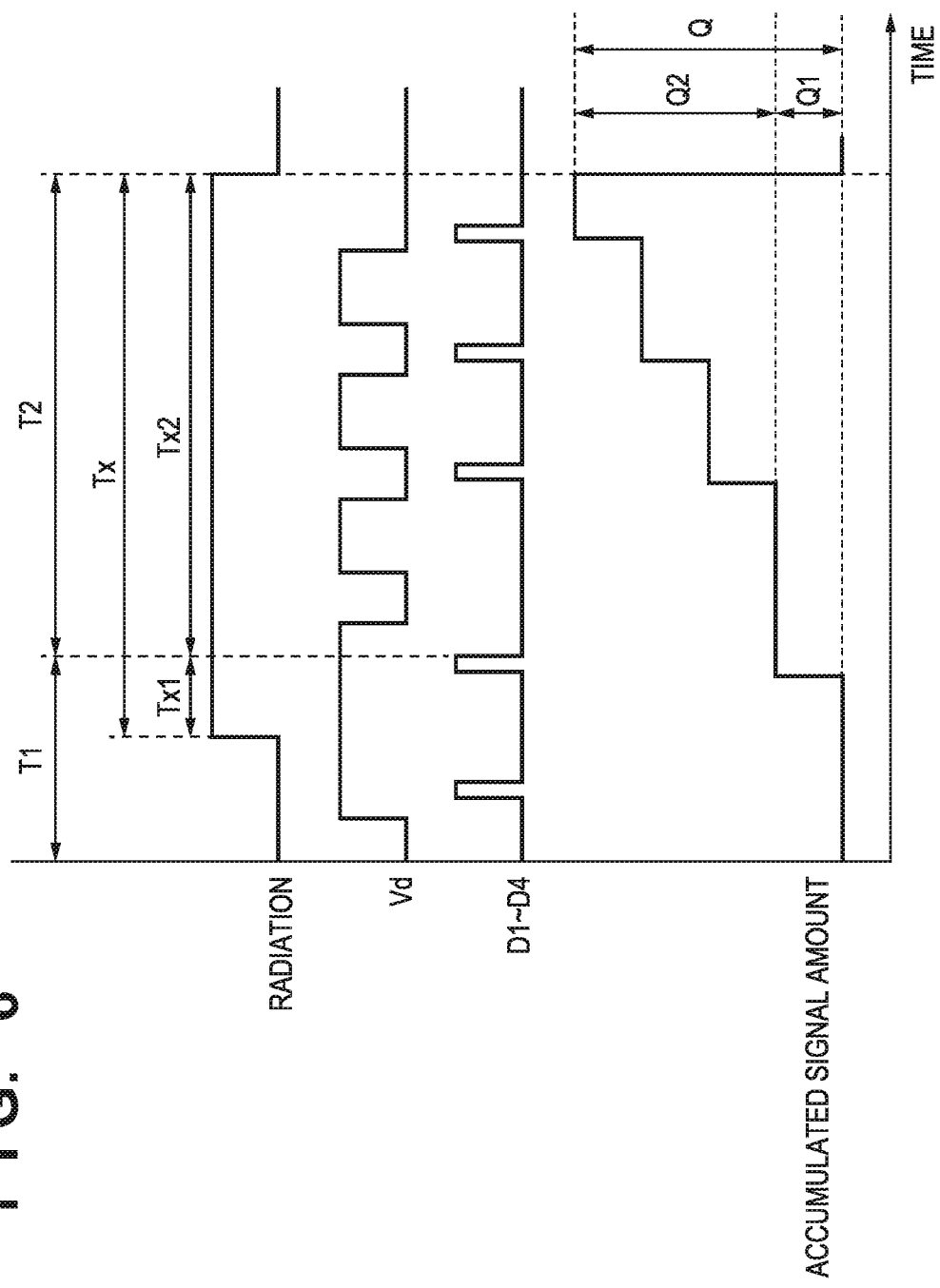
FIG. 6 is a conceptual view showing how signals at the time of detection of the start of irradiation are added when an integrated dose is measured.

Assume that in the period T1, signal electric charge accumulated in the conversion element 106 is directly read out to detect the start of irradiation with radiation, and the same detection pixel 102 is used to measure the integrated dose of incident radiation, as shown in FIG. 6. In this case, when the conversion element 106 and the detection signal line 112 are reset after the start of irradiation with radiation is detected in the period T1, the signal read out in the period T1 is reset. This degrades the quantitativity of the measurement of the integrated dose of radiation, which is executed in the period T2. Referring to FIG. 6, assume that a signal Q1 is a signal read out in the period T1, a signal Q2 is a signal read out in the period T2, and a signal Q is a signal accumulated in the periods T1 and T2. Because the signal Q1 is read out in the period T1, only the signal Q2 is read out in the period T2. Accordingly, the control unit 155 cannot accurately measure the integrated dose of radiation. This phenomenon is conspicuous when imaging is performed with high intensity of incident radiation for a short irradiation time of radiation. For this reason, in this embodiment, the control unit 155 can quantitatively measure the integrated dose of radiation by causing the memory unit 125 to temporarily store signals obtained at the time of detection of the start of irradiation with radiation in the period T1 and totalizing the signals at the time of integrated dose measurement in the period T2. In the arrangement shown in FIG. 1, the memory unit 125 is arranged independently of the control unit 155 and the readout unit 151. However, this is not exhaustive. For example, the memory unit 125 may be arranged in the control unit 155 or arranged in the processing circuit 151a of the readout unit 151. Furthermore, for example, the signal processing unit 124 may have the function of the memory unit 125.

In the arrangement shown in FIG. 1, signals from the detection units R1 to R4 of the ROIs are respectively output to the different detection signal lines 112. The control unit 155 can therefore cause the memory unit 125 to store a signal acquired at the time of detection of the start of irradiation with radiation for each ROI. A case in which signals are simultaneously output from a plurality of ROIs to the same detection signal line 112 will be described later in the second mode (to be described later). In addition, in the first mode as well, the control unit 155 may output, to the readout unit 151, composition signals obtained by composing signals from the detection units R1 to R4 of the ROIs and store the composition signals in the memory unit 125 at the time of detection of the start of irradiation with radiation. When measuring the integrated dose of incident radiation, the control unit 155 distributes composition signals stored in the memory unit 125 by using the same method as that in the second mode (to be described later) and measures the integrated dose of radiation incident on each ROI.

A period T3 in FIG. 5 will be described next. The period T3 is a period during which, after irradiation with radiation is complete, signals for a radiation image accumulated in the conversion elements 104 of the pixels 101 and the conversion elements 104' of the detection pixels 102 upon irradiation with radiation are read out. In order to scan the control lines 108, the control unit 155 controls the driving circuit 151b to sequentially apply the voltage Von to the signals Vg1 to Vg12, and transfers signals accumulated in the conversion elements 104 and 104' to the processing circuit 151a via the signal lines 110. In the period T3, the control unit 155 controls the driving circuit 151b to apply the voltage Voff to the signal Vd. In addition, in the period T3, the detection signal lines 112 may be connected to a fixed potential to prevent the detection signal lines 112 from floating.

The integrated dose of radiation incident on the conversion element 106 serving as a detection unit is acquired based on both a signal acquired at the time of performing an operation for detecting the start of irradiation with radiation and a signal acquired at the time of performing an operation for measuring the integrated dose of radiation. This can improve the quantitativity of the integrated dose of radiation incident on the conversion element 106 of the ROI serving as a detection unit of the radiation imaging apparatus 200 and improve the image quality of an obtained radiation image.

Figure 7:
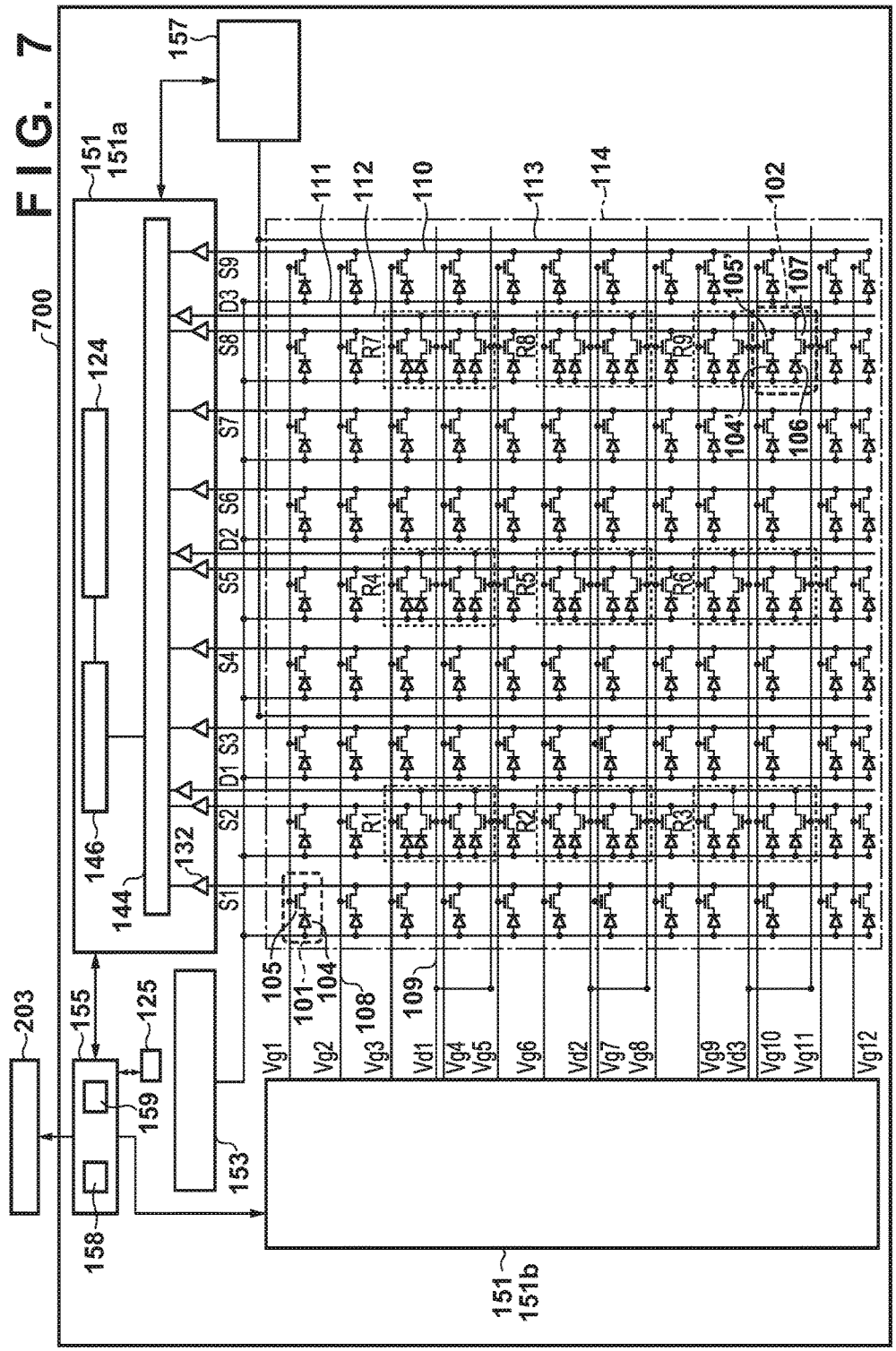
FIG. 7 is a view showing an example of the arrangement of a radiation imaging apparatus according to an embodiment of the present invention.

The second mode of this embodiment will be described next, in which a plurality of ROIs are connected to the same detection signal line 112, and signals are simultaneously output from the plurality of ROIs to the single detection signal line 112 at the time of detection of the start of irradiation with radiation. FIG. 7 shows an example of the arrangement of a radiation imaging apparatus 700. The radiation imaging apparatus 700 is provided with ROIs in nine places (detection units R1 to R9). In order to correct crosstalk caused when the start of irradiation with radiation is detected and the integrated dose of radiation is measured, correction lines 113 and a crosstalk correction circuit 157 that reads out signals from the correction lines 113 are arranged in the radiation imaging apparatus 700. Other arrangements may be the same as those of the radiation imaging apparatus 200 described above.

In the arrangement shown in FIG. 7, pixels 101 and detection pixels 102 are arranged in 12 rows×9 columns in an image sensing region 114. As described above, the image sensing region 114 is provided with nine ROIs as detection units that monitor radiation. The two detection pixels 102 are arranged in each ROI. Accordingly, two conversion elements 106 of the two detection pixels 102 included in one ROI serve as one detection unit for monitoring incident radiation. Of the nine ROIs, the detection pixels 102 of detection units R1, R2, and R3 are connected to a detection signal line 112 (D1). The detection pixels 102 of detection units R4, R5, and R6 are connected to a detection signal line 112 (D2). The detection pixels 102 of detection units R7, R8, and R9 are connected to a detection signal line 112 (D3). In this specification, a plurality of ROIs connected to the same detection signal line 112 are sometimes called a detection unit group. In the arrangement shown in FIG. 7, in the image sensing region 114, three detection unit groups are arranged, which are respectively a detection group including the detection units R1, R2, and R3, a detection group including the detection units R4, R5, and R6, and a detection group including the detection units R7, R8, and R9.

Figure 8:
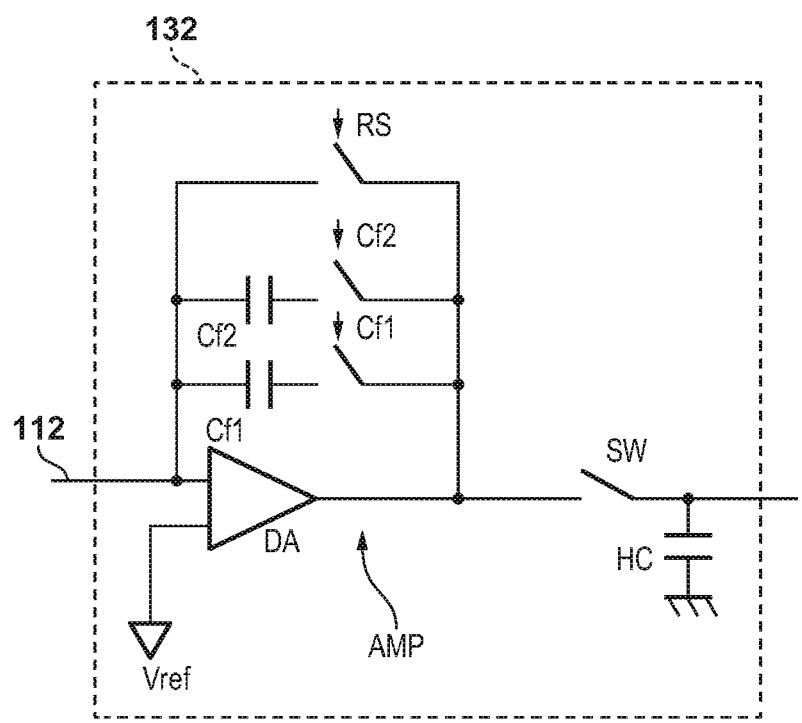
FIG. 8 is a circuit diagram showing an example of the arrangement of a sensing unit of the radiation imaging apparatus in FIG. 7.

The arrangement of a sensing unit 132 will be described next with reference to FIG. 8. The sensing unit 132 includes an amplification circuit AMP, a holding capacitor HC, and a sampling switch SW. The amplification circuit AMP includes a differential amplifier DA including a first input terminal, a second input terminal, and an output terminal, feedback capacitors Cf1 and Cf2 provided in parallel between the first input terminal and the output terminal, and a reset switch (reset unit) RS. The detection signal line 112 is connected to the first input terminal, and a reference potential Vref is supplied to the second terminal. The sampling switch SW is arranged between the output terminal of the differential amplifier DA (amplification circuit AMP) and the holding capacitor HC. In this case, the sensing unit 132 according to this embodiment has a plurality of feedback capacitors Cf. This makes it possible to read out signals output to the detection signal line 112 with a plurality of different gains. In detecting the start of irradiation with radiation, in order to read out signals with high sensitivity, signals output from the conversion elements 106 of the detection pixels 102 of a plurality of ROIs are simultaneously read out. In contrast to this, in measuring the integrated dose of radiation, because a resolution is required for each ROI, a signal needs to be read out for each ROI. In order to totalize signals acquired at the time of detection of the start of irradiation with radiation in the measurement of the integrated dose of radiation as in the first mode, in particular, quantitativity is required in detecting the start of irradiation with radiation. For this reason, in detecting the start of irradiation with radiation, the value of the feedback capacitor Cf is increased so as not to saturate the feedback capacitor Cf. In contrast to this, in measuring the integrated dose of radiation, because signals that can be acquired are small, the value of the feedback capacitor Cf is reduced. For this reason, the sensing unit 132 according to this embodiment is provided with a plurality of feedback capacitors Cf. When detecting the start of irradiation with radiation, for example, a control unit 155 sets the switch of the feedback capacitor Cf1 (large capacitance) with a low gain in the conduction state (ON state) and sets the switch of the feedback capacitor Cf2 (small capacitance) with a high gain in the nonconduction state (OFF state). Thereafter, upon detecting the start of irradiation with radiation, the control unit 155 sets the switch of the high-gain feedback capacitor Cf2 in the conduction state and sets the switch of the low-gain feedback capacitor Cf1 in the OFF state at the time of measurement of the integrated dose of radiation. Providing a plurality of feedback capacitors Cf and switching them as needed in this manner can detect the start of irradiation with radiation with high sensitivity and implement quantitative detection. This also makes it possible to execute subsequent measurement of the integrated dose of radiation with high accuracy.

The operation of the radiation imaging apparatus 700 according to this embodiment will be described next with reference to the timing chart of FIG. 9. In a period T1, the control unit 155 executes the operation of acquiring signals simultaneously output from the detection units R1 to R9 to a readout unit 151 and detecting the start of irradiation with radiation. The control unit 155 controls a driving circuit 151b to apply a voltage Von to signals Vd1 to Vd3, and fixes switch elements 107 of the detection pixels 102 to the conduction state. For this reason, the control unit 155 causes the readout unit 151 to output signals from the plurality of detection units R1 to R3 via the detection signal line 112 (D1), and causes a processing circuit 151a to output composition signals obtained by composing the signals simultaneously output from the detection units R1 to R3. In addition, the control unit 155 causes the readout unit 151 to output composition signals obtained by composing signals from the plurality of detection units R4 to R6. Likewise, the control unit 155 causes the readout unit 151 to output composition signals obtained by composing signals from the plurality of detection units R7 to R9. In this embodiment, the control unit 155 detects the start of irradiation with radiation based on these three composition signals. For example, the control unit 155 may determine that the start of irradiation has been detected when one of the three composition signals has exceeded a predetermined value or may determine that the start of irradiation has been detected when the value obtained by totalizing the three composition signals has exceeded a predetermined value. At this time, the control unit 155 causes the readout unit 151 (processing circuit 151a) to read out a composition signal by using the low-gain feedback capacitor Cf1 as the feedback capacitor Cf of the sensing unit 132, thereby preventing the feedback capacitor Cf from being saturated. The control unit 155 causes a memory unit 125 to store such composition signal for each detection unit group before the conversion elements 106 of the detection pixels 102 and the detection signal line 112 are reset, in order to detect the start of irradiation with radiation and measure the integrated dose of radiation in the period T2.

After causing the memory unit 125 to store the composition signal for each detection unit group, the control unit 155 controls the driving circuit 151b to intermittently apply the voltage Von to the signals Vd1 to Vd3 so as to intermittently set the switch elements 107 of the detection pixels 102 in the conduction state in the period T2. With this operation, the control unit 155 acquires a signal for each of the detection units R1 to R9 (each of a plurality of signals including a signal from the detection unit R1, a signal from the detection unit R2, . . . , a signal from the detection unit R9), which is individually read out from each of the detection units R1 to R9 to the readout unit 151. In addition, the control unit 155 controls the driving circuit 151b to always apply a voltage Voff to signals Vg1 to Vg12, thereby setting switch elements 105 in the nonconduction state and accumulating electric charge corresponding to incident radiation in conversion elements 104 and 104'. At this time, in order to accurately measure the integrated dose of radiation, the control unit 155 causes the readout unit 151 (processing circuit 151a) to read out signals by using the high-gain feedback capacitor Cf2 as the feedback capacitor Cf of the sensing unit 132.

In the second mode, the control unit 155 executes more quantitative measurement of the integrated dose of radiation by using signals acquired at the time of detection of the start of irradiation with radiation in the period T1 and stored in the memory unit 125 and signals acquired at the time of integrated dose measurement in the period T2. In the second mode, the feedback capacitors Cf of the sensing unit 132 are switched between the detection of the start of irradiation with radiation and integrated dose measurement. In addition, when detecting the start of irradiation with radiation, the control unit 155 acquires the composition signal obtained by composing signals output from the conversion elements 106 of the detection pixels 102 of a plurality of ROIs for each detection unit group. The next will describe a method of adding and totalizing the composition signals acquired by the control unit 155 at the time of detection of the start of irradiation with radiation and signals individually output from the detection units R1 to R9 at the time of measurement of the integrated doses of radiation.

For example, the composition signals output from the conversion elements 106 of the plurality of ROIs included in the respective detection unit groups, which are obtained at the time of detection of the start of irradiation with radiation in the period T1, are set as follows:

the composition signal from the detection unit group (the detection units R1, R2, and R3) connected to the detection signal line 112 (D1): X;

the composition signal from the detection unit group (the detection units R4, R5, and R6) connected to the detection signal line 112 (D2): Y; and the composition signal from the detection unit group (the detection units R7, R8, and R9) connected to the detection signal line 112 (D3): Z In addition, the signals obtained from the conversion elements 106 of the respective ROIs at the time of measurement of the integrated doses of radiation in the period T2 are set as follows:

the signal from the detection unit R1: x1
the signal from the detection unit R2: x2
the signal from the detection unit R3: x3
the signal from the detection unit R4: y1
the signal from the detection unit R5: y2
the signal from the detection unit R6: y3
the signal from the detection unit R7: z1
the signal from the detection unit R8: z2
the signal from the detection unit R9: z3

Furthermore, the values of the feedback capacitors Cf1 and Cf2 are set as follows:

feedback capacitor Cf1: C1
feedback capacitor Cf2: C2

In order to use the composition signals acquired at the time of detection of the start of irradiation with radiation for the measurement of the integrated doses of radiation, it is necessary to distribute the composition signals simultaneously output from the plurality of ROIs for the respective detection units to the signal components output from the conversion elements 106 of the respective ROIs. For this purpose, the control unit 155 decides, for each detection unit group, a signal component, of a composition signal, which is output from the conversion element 106 of a selected ROI in accordance with the ratio of a signal output at the time of measurement of an integrated dose from a selected ROI of a plurality of ROIs to the sum of signals output from the respective ROIs. For example, consider the detection units R1 to R3 connected to the same detection signal line 112 (D1). The control unit 155 distributes the composition signal X from the detection units R1 to R3, stored in the memory unit 125, in accordance with the ratio of the signal x1 output from the selected detection unit R1 to the sum of the signals x1 to x3 read out from the detection units R1 to R3 at the time of integrated dose measurement. With this operation, the control unit 155 decides the signal component output from the conversion element 106 of the selected detection unit R1 of the detection units R1 to R3. The control unit 155 can sequentially or concurrently select ROIs of the plurality of ROIs of each detection unit group and decide the signal component output from the conversion element 106 of the selected ROI. The control unit 155 also performs correction in accordance with the operation of reading out signals with different gains by switching the feedback capacitors Cf. For example, consider the detection unit R1 among the detection units R1 to R9. Letting S1 be the sum of signals obtained at the time of detection of the start of irradiation with radiation and at the time of measurement of the integrated dose of radiation in the detection unit R1, S1 is given by $$S1 = \Sigma x1 + [X \times (C1/C2) \times \{x1/(x1+x2+x3)\}] \quad (1)$$

With regard to the detection units R2 to R9 of the ROIs, the control unit 155 can decide signal components output from the conversion elements 106 of the respective selected ROIs by using equation (1). The signals x1 to z3 from the detection units R1 to R9 which are used to decide such signal components each may be a signal, of the signals intermittently output from each ROI, which is obtained by one output operation or the sum of signals obtained from each ROI by several output operations.

The control unit 155 acquires the integrated dose of radiation incident on the selected detection unit R1 based on the decided signal component from the selected detection unit (the detection unit R1 in this case) and the signal x1, of the signals individually read out from the plurality of detection units R1 to R3 at the time of measurement of the integrated doses of radiation, which is output from the selected detection unit R1. More specifically, the control unit 155 corrects the signal component, of the composition signal X, which is decided as being output from the detection unit R1 in accordance with the ratio (C1/C2) between the gain used in the readout operation for the detection of the start of irradiation with radiation and the gain used in the readout operation for integrated dose measurement. The control unit 155 acquires the integrated dose of radiation based on the sum of this corrected signal component and the signal x1, of the signals individually read out from the plurality of detection units R1 to R3 at the time of measurement of the integrated dose of radiation, which is output from the selected detection unit R1. When signals are read out by using the same gain (without changing the feedback capacitor Cf of the sensing unit 132) at the time of detection of the start of irradiation with radiation and at the time of integrated dose measurement, the control unit 155 need not correct the signal component in accordance with a gain ratio. In this case, the control unit 155 acquires the integrated dose of radiation based on the sum of the signal component decided as being output from the detection unit R1 and the signal x1, of the signals individually read out from the plurality of detection units R1 to R3 at the time of measurement of the integrated dose of radiation, which is output from the selected detection unit R1. The control unit 155 can determine, based on the acquired integrated dose of radiation, whether to stop exposure to radiation. Upon determining that the integrated dose of radiation has reached a predetermined value, the control unit 155 outputs a signal for stopping exposure to radiation in accordance with the determination result. The radiation source 205 stops exposure to radiation in accordance with this signal.

Upon completion of irradiation with radiation, in the period T3, the control unit 155 causes the readout unit 151 to read out signals for a radiation image which are accumulated in the conversion element 104 of the pixel 101 and the conversion element 104' of the detection pixel 102 based on radiation. In order to scan the control lines 108, the control unit 155 controls the driving circuit 151b to sequentially apply the voltage Von to the signals Vg1 to Vg12, and sequentially transfers, to the processing circuit 151a, the signals accumulated in the conversion elements 104 and 104' via signal lines 110. Reflecting the signals acquired at the time of detection of the start of irradiation with radiation in the signals obtained at the time of acquisition of integrated doses makes it possible to improve the quantitativity at the time of measurement of the integrated doses of radiation incident on the respective ROIs of the radiation imaging apparatus 700 and improve the quality of an obtained radiation image.

In the periods T1 and T2, in order to read out signals during irradiation with radiation, signals are read out while the potentials of individual electrodes 311 of the conversion elements 104 and 104' fluctuate. In this case, crosstalk is caused by the capacitive coupling between the individual electrodes 311 of the conversion elements 104 and 104' and the detection signal lines 112. In order to correct crosstalk caused between the period T1 and the period T2, the correction lines 113 may be arranged adjacent to the detection signal lines 112. In this case, "adjacent" indicates a region in which almost the same crosstalk as crosstalk occurring at a given detection signal line 112 occurs. With this operation, almost the same crosstalk as crosstalk occurring at the detection signal line 112 is transferred from the correction lines 113 to the crosstalk correction circuit 157. The control unit 155 can reduce the influence of crosstalk by subtracting crosstalk read out by the crosstalk correction circuit 157 from a signal read out to the processing circuit 151a by the readout unit 151.

Figure 10:
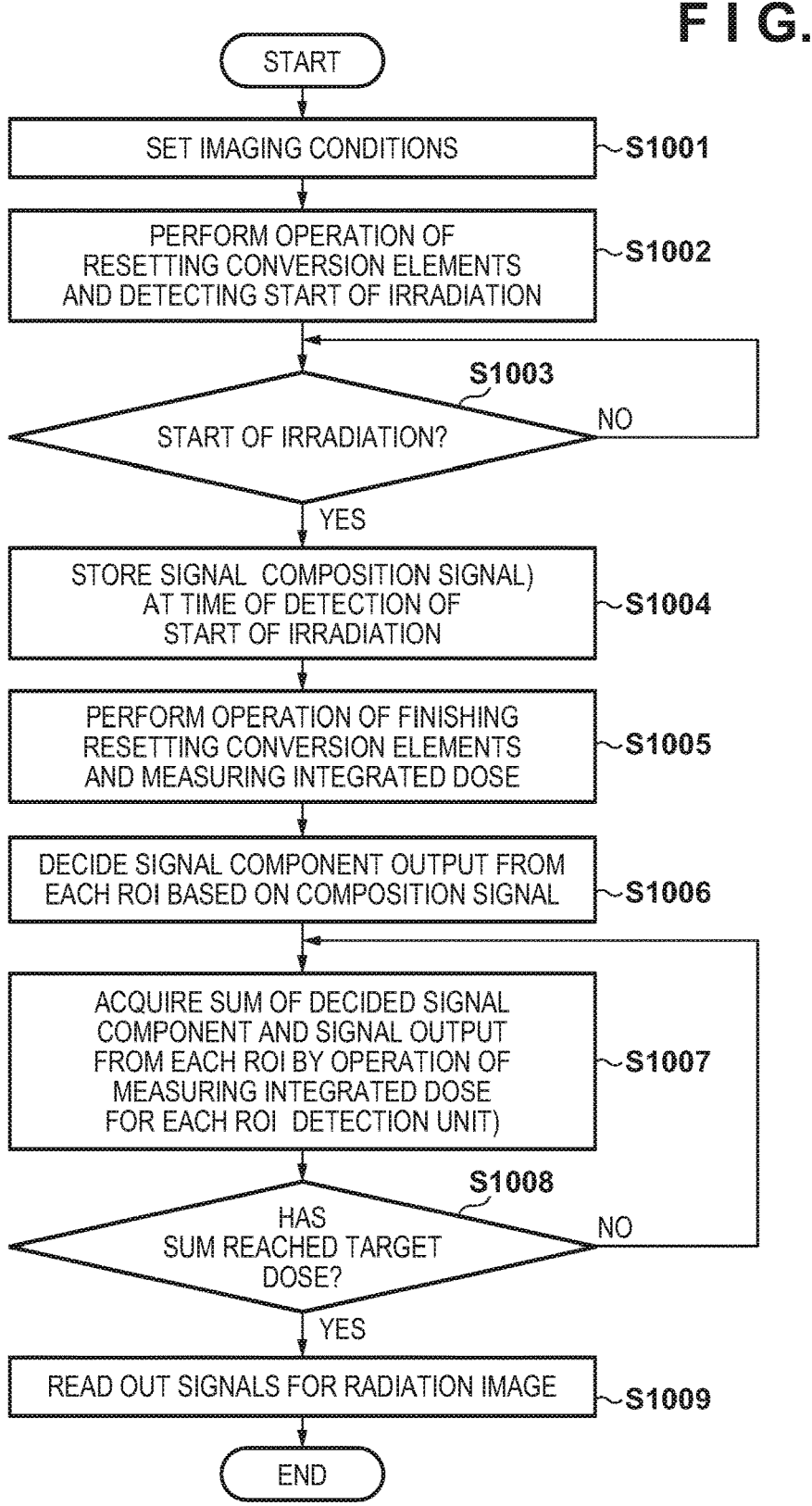
FIG. 10 is a flowchart showing the operation of the radiation imaging apparatus in FIG. 7.

FIG. 10 is a flowchart for explaining the operation of the radiation imaging apparatus 700. First of all, in step S1001, the control unit 155 acquires the imaging information input to a controller 202 by a user such as a doctor or technician via an interface 203. The imaging information can include the target integrated dose of radiation, the irradiation time of radiation, the tube current and tube voltage of a radiation source 205, and the set position of an ROI as a detection unit that monitors radiation. The control unit 155 then sets imaging conditions by, for example, reading out an operation program suitable for the imaging information input to the controller 202 from a memory 158 to a CPU 159.

Figure 9:
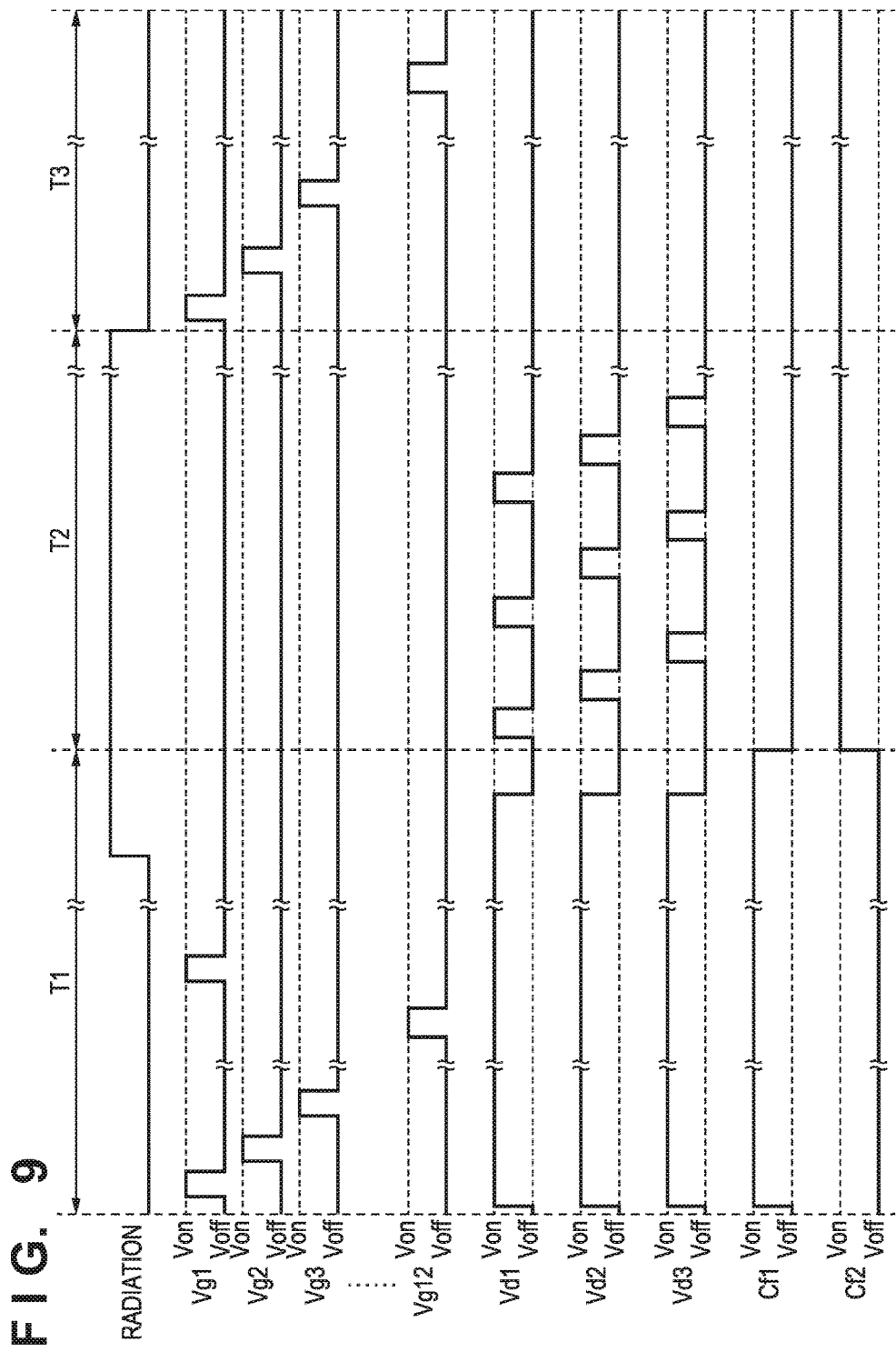
FIG. 9 is a timing chart showing the operation of the radiation imaging apparatus in FIG. 7.

Upon setting the imaging conditions, the control unit 155 shifts to step S1002 to start the operation of acquiring signals simultaneously read out from the detection units R1 to R9 by the readout unit 151, which are indicated in the period T1 in FIG. 9, and detecting the start of irradiation with radiation. More specifically, the control unit 155 controls the driving circuit 151b to fix the signals Vd1 to Vd3 to the voltage Von, and sets the switch element 107 of the detection pixel 102 in the conduction state. The readout unit 151 simultaneously reads out signals from the plurality of detection units R1 to R3 to the processing circuit 151a via the detection signal line 112 (D1) under the control of the control unit 155. This makes the control unit 155 acquire the composition signal obtained by composing the signals output from the detection units R1 to R3. The control unit 155 acquires the composition signal obtained by composing the signals simultaneously read out from the plurality of detection units R4 to R6 to the processing circuit 151a via the detection signal line 112 (D2). Likewise, the control unit 155 acquires the composition signal obtained by composing the signals simultaneously read out from the plurality of detection units R7 to R9 to the processing circuit 151a via the detection signal line 112 (D3). In addition, the control unit 155 controls the driving circuit 151b to sequentially apply the voltage Von to control lines 108 (signals Vg1 to Vg12), and starts to reset the conversion element 104 of the pixel 101 and the conversion element 104' of the detection pixel 102.

The control unit 155 then determines, based on the composition signal acquired for each detection unit group, in step S1003 whether the start of irradiation with radiation is detected. For example, the control unit 155 determines that irradiation with radiation has started, in accordance with when the acquired composition signal has exceeded a predetermined value. Upon detecting the start of irradiation with radiation, the control unit 155 shifts to step S1004 to cause the memory unit 125 to store, for each detection unit group, a composition signal output from the conversion elements 106 of a plurality of ROIs included in the respective detection unit groups used for the determination of the start of irradiation with radiation. The procedure from step S1002 to step S1004 corresponds to the period T1 shown in FIG. 9.

Upon causing the memory unit 125 to store the composition signals, the control unit 155 shifts to step S1005 to start the operation indicted in the period T2 in FIG. 9. The control unit 155 controls the driving circuit 151b to always apply the voltage Voff to the signals Vg1 to Vg12, causes the switch elements 105 and 105' to finish reset operations, and causes the conversion elements 104 and 104' to accumulate electric charge corresponding to incident radiation. In addition, the control unit 155 controls the driving circuit 151b to intermittently apply the voltage Von to the signals Vd1 to Vd3 so as to intermittently set the switch elements 107 of the detection pixels 102 in the conduction state. The control unit 155 detects the doses of radiation incident on the conversion elements 106 of the respective ROIs in real time by causing the conversion elements 106 of the detection units R1 to R9 to individually and intermittently output signals for each of the detection units R1 to R9. The control unit 155 starts measuring the integrated dose of incident radiation by integrating the doses of radiation incident on the conversion elements 106 of the detection units R1 to R9.

In step S1006, the control unit 155 then distributes composition signals for the respective detection unit groups, acquired at the time of detection of the start of irradiation with radiation and stored in the memory unit 125, to signal components for the respective ROIs included in the detection unit groups by using equation (1) described above. The control unit 155 decides signal components, of the composition signal X, which are output from the detection units R1, R2, and R3 in accordance with the ratios of signals x1, x2, and x3 to the sum of the signals x1, x2, and x3 individually read out from the plurality of detection units R1 to R3 at the time of integrated dose measurement. Likewise, the control unit 155 decides signal components, of the composition signal Y, which are output from the detection units R4, R5, and R6 in accordance with the ratios of signals y1, y2, and y3 to the sum of the signals y1, y2, and y3 individually read out from the plurality of detection units R4 to R6. In addition, likewise, the control unit 155 decides signal components, of the composition signal Z, which are output from the detection units R7, R8, and R9 in accordance with the ratios of signals z1, z2, and z3 to the sum of the signals z1, z2, and z3 individually read out from the plurality of detection units R7 to R9.

In step S1007, in integrated dose measurement, the control unit 155 acquires the integrated dose of radiation incident on the conversion element 106 of each ROI based on the signal output individually for each ROI and the signal component distributed to each ROI. At this time, as described above, upon causing the readout unit 151 to read out, with different gains, signals for the detection of the start of irradiation with radiation and signals for integrated dose measurement, the control unit 155 corrects signal components with the ratios of the respective gains. The control unit 155 then acquires the integrated dose of radiation based on the sum of the corrected signal components and the signals individually read out for the respective ROIs at the time of measurement of the integrated doses of radiation.

The control unit 155 can determine in step S1008, based on the integrated dose acquired in step S1007, whether to stop exposure to radiation. In accordance with the exposure stop determination result, the control unit 155 outputs a signal for stopping exposure to radiation. For example, the control unit 155 may output a signal for stopping exposure upon determining that the integrated dose of radiation has reached the target dose set in step S1001. In addition, for example, the control unit 155 may acquire the time when the integrated dose reaches the target dose set in step S1001 based on a temporal change in the integrated dose of radiation and output a signal for stopping exposure in accordance with the acquired time. The signal for stopping exposure to radiation, which is output from the control unit 155, is input to the radiation source 205 via the interface 203 and the radiation source interface 204. The radiation source 205 then stops irradiation with radiation. The control unit 155 may output a signal for stopping exposure to radiation when, for example, the integrated dose acquired from any one of a plurality of ROIs has reached a target dose. Alternatively, for example, target doses may be respectively set for a plurality of ROIs, so that when the integrated doses in all the ROIs reach the respective target doses, the control unit 155 outputs a signal for stopping exposure to radiation. Upon outputting a signal for stopping exposure to radiation, the control unit 155 shifts to step S1009. The procedure from step S1005 to step S1008 corresponds to the period T2 shown in FIG. 9.

In step S1009, the control unit 155 performs the operation indicated by the period T3 in FIG. 9. More specifically, the control unit 155 controls the driving circuit 151b to sequentially apply the voltage Von to the signals Vg1 to Vg12 to scan the control lines 108, and transfers the signals accumulated in the conversion elements 104 and 104' to the processing circuit 151a via the signal lines 110. With this operation, the control unit 155 reads out the signals for a radiation image accumulated in the conversion elements 104 of the pixels 101 and the conversion elements 104' of the detection pixels 102 in accordance with incident radiation.

Figure 11:
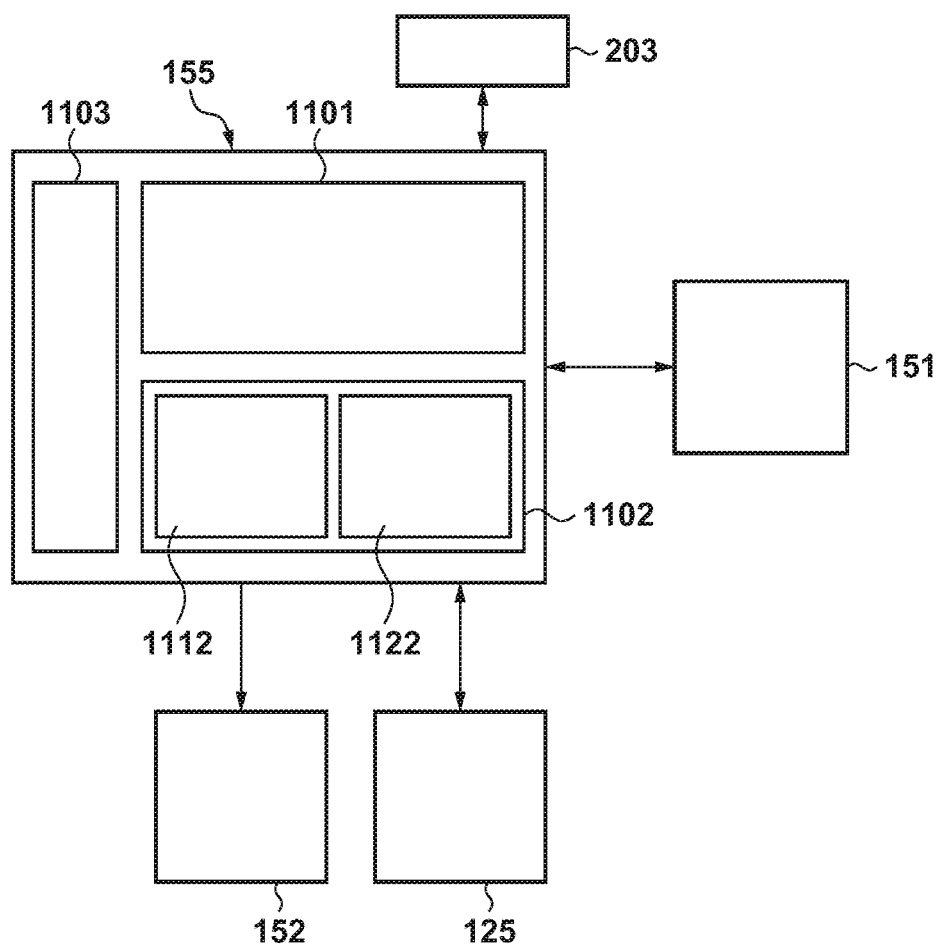
FIG. 11 is a view showing an example of the arrangement of a control unit of the radiation imaging apparatus in FIG. 7.

The control unit 155 is not limited to the arrangement including the CPU 159 and the memory 158, and may have an arrangement including a drive control unit 1101, an exposure control unit 1102, and a setting unit 1103, as shown in FIG. 11, to execute the respective steps described above. In step S1001, the setting unit 1103 acquires imaging information input by the user to the controller 202 via the interface 203. The setting unit 1103 sets driving conditions for the drive control unit 1101 and the exposure control unit 1102 in accordance with imaging information. In steps S1002 to S1004, the drive control unit 1101 causes the conversion elements 104 and 104' to perform reset operations, and acquires a composition signal from the conversion element 106 of the detection pixel 102 selected as an ROI to detect the start of irradiation with radiation.

In steps S1005 to S1008, the drive control unit 1101 then causes the conversion elements 104 and 104' to accumulate electric charge corresponding to incident radiation. The drive control unit 1101 also causes the conversion element 106 of each ROI to individually and intermittently output signals. The exposure control unit 1102 includes a distribution unit 1112 and a determination unit 1122. The distribution unit 1112 decides the signal components output from the respective ROIs based on the composition signal stored in the memory unit 125 in accordance with the ratios of signals individually output from the conversion elements 106 of the respective ROIs. The determination unit 1122 determines whether to stop exposure to radiation, based on the sum of the signals output from the conversion elements 106 of the respective ROIs and the signal components decided by the distribution unit 1112. Upon determining that the integrated dose of radiation has reached the target dose set in step S1001, the determination unit 1122 outputs a signal for stopping exposure. Upon outputting a signal for stopping exposure, the determination unit 1122 shifts to step S1009, in which the drive control unit 1101 reads out signals for generating a radiation image which are accumulated in the conversion elements 104 of the pixels 101 and the conversion elements 104' of the detection pixels 102.

Assume that a plurality of ROIs are connected to one detection signal line 112. In this case, at the time of detection of the start of irradiation with radiation, the control unit 155 acquires the composition signal obtained by composing the signals simultaneously (concurrently) output from the conversion elements of the respective ROIs by the readout unit 151. In this case as well, the control unit 155 distributes the composition signal in accordance with the signals individually output from the respective ROIs read out by the readout unit 151 at the time of integrated dose measurement, and decides the distributed signal components as the signal components outputs from the respective ROIs. The control unit 155 acquires the integrated dose of incident radiation by using these signal components and the signals individually output from the respective ROIs, thereby improving the quantitativity of the integrated dose of radiation incident on the ROIs of the radiation imaging apparatus 700. In addition, the sensing unit 132 reads out signals with different gains at the time of detection of the start of irradiation with radiation and at the time of measurement of the integrated dose of incident radiation. This makes it possible to detect the start of irradiation with radiation with high sensitivity and implement quantitative detection. In addition, it is possible to accurately measure the integrated dose of radiation. Furthermore, arranging the correction lines 113 and the crosstalk correction circuit 157 makes it possible to reduce the influence of crosstalk.

Figure 12:
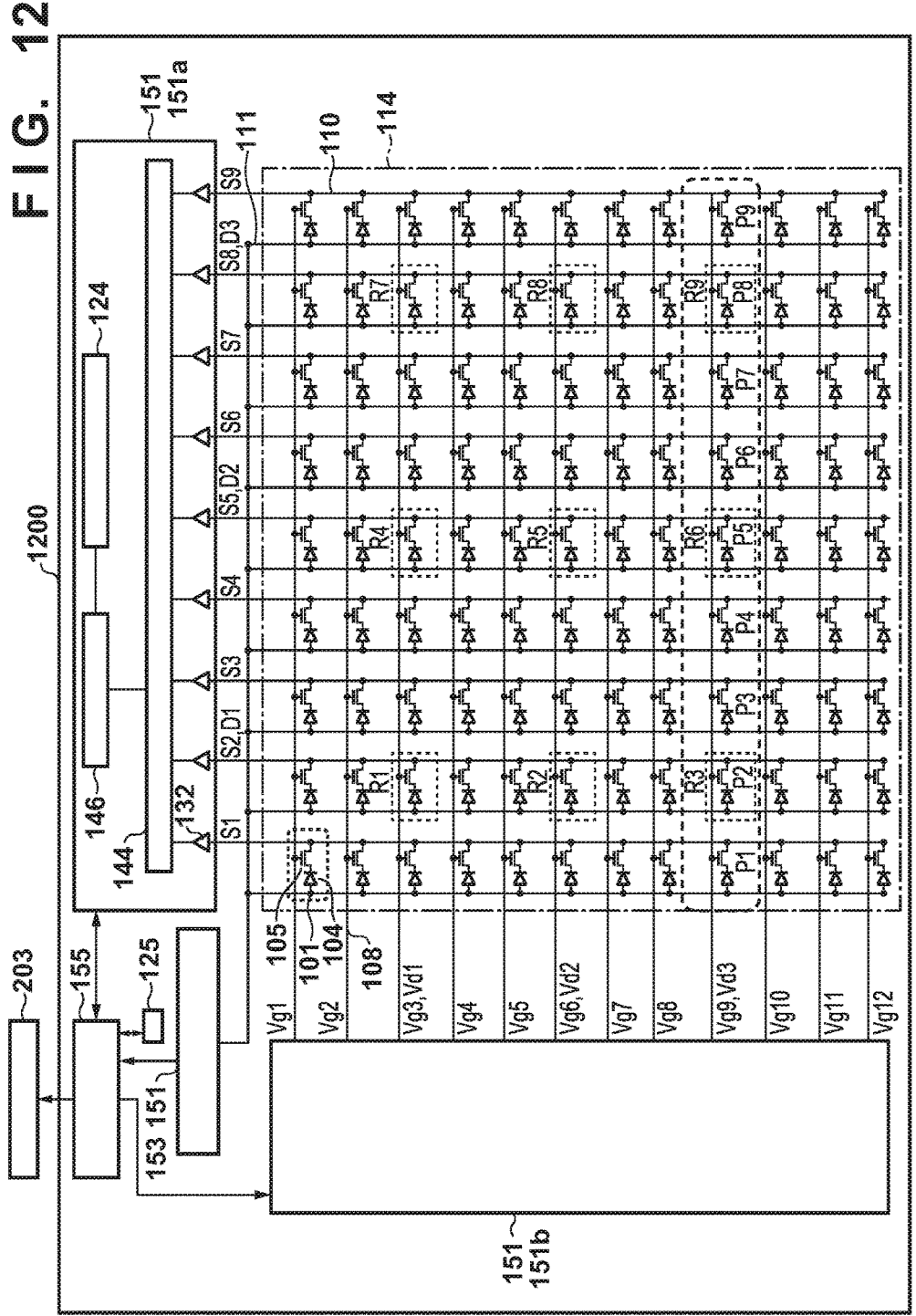
FIG. 12 is a view showing an example of the arrangement of a radiation imaging apparatus according to an embodiment of the present invention.
Figure 13:
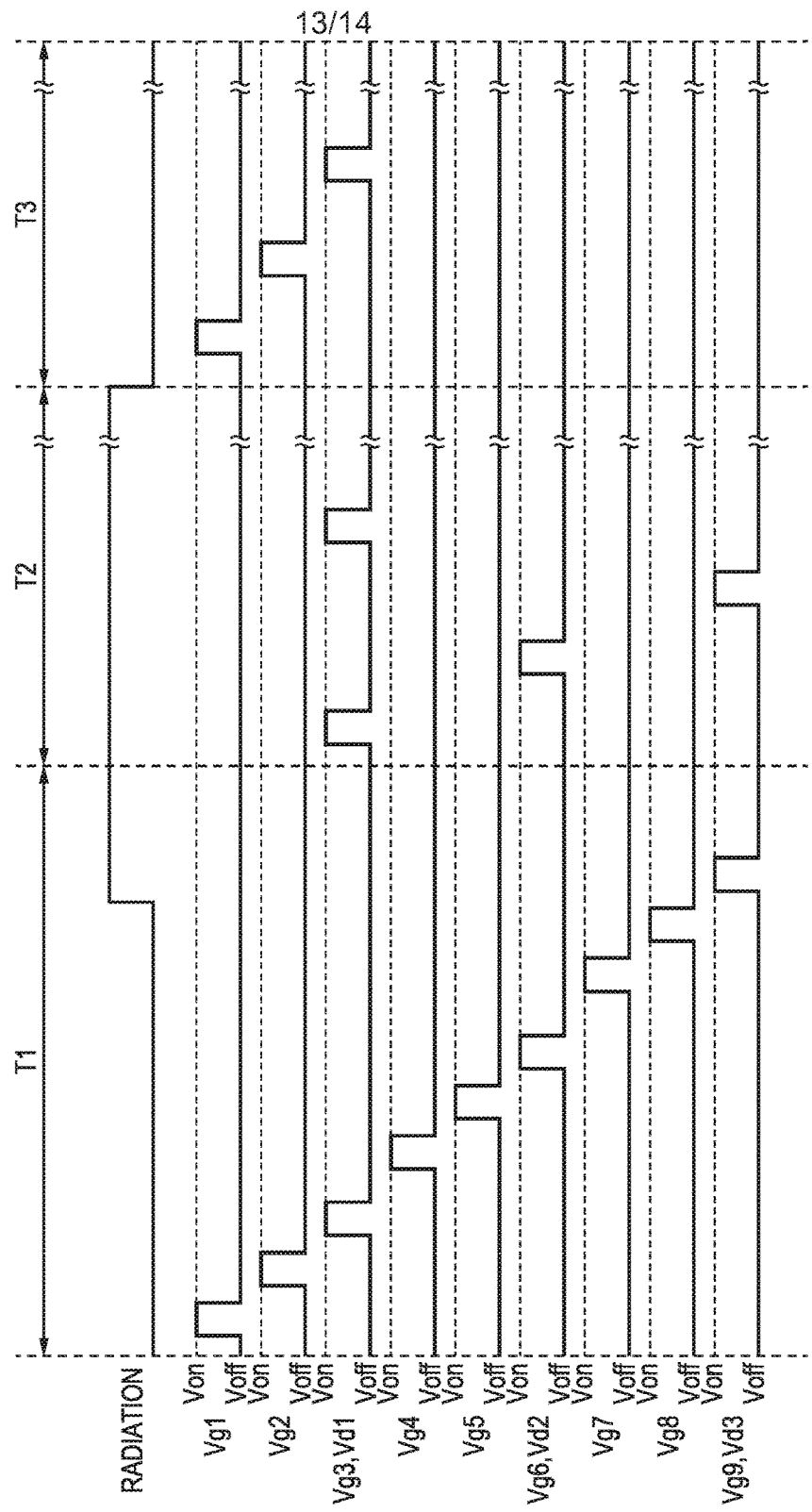
FIG. 13 is a timing chart showing the operation of the radiation imaging apparatus in FIG. 11.

The arrangement of a radiation imaging apparatus according to an embodiment of the present invention will be described with reference to FIGS. 12 and 13. FIG. 12 shows an example of the arrangement of a radiation imaging apparatus 1200 according to the second embodiment of the present invention. This apparatus differs from the above radiation imaging apparatuses 200 and 700 in that it reads out signals obtained from bias wirings 111 by using a bias power supply 153 at the time of detection of the start of irradiation with radiation, and does not have any of the detection pixels 102. Other arrangements may be the same as those in the first embodiment described above.

In the arrangement shown in FIG. 12, pixels 101 are arranged in 12 rows×9 columns in an image sensing region 114. Although any of the detection pixels 102 are not arranged in the image sensing region 114 unlike the arrangement described above, conversion elements 104 of some of the plurality of pixels 101 serve as detection units. The conversion elements 104 serving as detection units may be any of the conversion elements 104. Such conversion elements may be decided as needed depending on the placement of an object. In the arrangement shown in FIG. 12, ROIs serving as detection units for monitoring radiation are nine detection units R1 to R9.

The operation of the radiation imaging apparatus 1200 according to this embodiment will be described next with reference to the timing chart of FIG. 13. In a period T1, a control unit 155 controls a driving circuit 151b to sequentially apply a voltage Von to signals Vg1 to Vg12, and periodically resets individual electrodes 311 of the pixels 101 to a constant potential. In this case, when the voltage Von is applied to signals Vg3(Vd1), Vg6(Vd2), and Vg9 (Vd3) that control the conversion elements 104 set as ROIs, electric charge flows from the pixels 101 corresponding to the respective ROIs (the detection units R1 to R9) to signal lines 110. At this time, as the electric charge flows, electric charge also flows (current is generated) in the bias wirings 111 via switch elements 105. In this embodiment, the control unit 155 monitors changes in current in the bias wirings 111 via the bias power supply 153 to detect the start of irradiation with radiation. That is, in the embodiment, the bias power supply 153 serves as part of a readout unit 151. At this time, the signal obtained by applying the voltage Von to the signal Vg3(Vd1) can be a composition signal obtained by composing signals output from the conversion elements 104 of the pixels 101 connected to a control line 108 (Vg3 (Vd1)), which include the detection units R1, R4, and R7 of the ROIs. Upon detecting the start of irradiation with radiation, the control unit 155 causes a memory unit 125 to store the composition signal obtained by monitoring the bias power supply 153.

Upon detecting the start of irradiation with radiation, in a period T2, the control unit 155 controls the driving circuit 151b to sequentially apply the voltage Von to the signals Vg3(Vd1), Vg6(Vd2), and Vg9(Vd3), and measures the integrated dose of incident radiation. By intermittently setting the switch elements 105 of the pixels 101 set as ROIs in the conduction state, the control unit 155 acquires signals individually output from the respective ROIs via a processing circuit 151a. In addition, the control unit 155 controls the driving circuit 151b to always apply a voltage Voff to the signals Vg1, Vg2, Vg4, Vg5, Vg7, and Vg8. This sets, in the nonconduction state, the switch elements 105 of the pixels 101 other than those on a row which are set as ROIs, and accumulates electric charge corresponding to incident radiation in the respective conversion elements 104.

In this embodiment as well, the control unit 155 uses the composition signals acquired at the time of detection of the start of irradiation with radiation in the period T1 and stored in the memory unit 125 when performing integrated dose measurement in the period T2, thereby executing more quantitative measurement of the integrated dose of radiation. In this case, consider the timing when the signal Vg9(Vd3) is set at the voltage Von. When the signal Vg9(Vd3) is set at the voltage Von in the period T1, signals are output from the conversion elements 104 of the three pixels 101 of the detection units R3, R6, and R9, and signals are also output from the conversion elements 104 of the other pixels 101 connected to the control line 108 (Vg9(vd3)). The output signals are then composed. In the period T2, the control unit 155 decides signal components, of the composition signal acquired in the period T1, which are output from the respective ROIs in accordance with the ratios of the signals output from the conversion elements 104 of the respective pixels 101 connected to the control line 108 (Vg9(Vd3)).

Let "X" be the signal that the control unit 155 has acquired via the bias power supply 153 at the timing when the signal Vg9(Vd3) is set at the voltage Von in the period T1. In addition, outputs from the conversion elements 104 of the pixels 101 (P1 to P9) connected to the control line 108 (Vg9(Vd3)) which the control unit 155 has acquired at the timing when the signal Vg9(Vd3) is set at the voltage Von in the period T2 are represented as follows:

pixel P1: x1
pixel P2 (detection unit R3): x2
pixel P3: x3
pixel P4: x4
pixel P5 (detection unit R6): x5
pixel P6: x6
pixel P7: x7
pixel P8 (detection unit R9): x8
pixel P9: x9

In this case, for example, the signal component "s3", of the signal "X" obtained in the period T1, which is obtained by the detection unit R3 is given by $$s3 = X \times \{x2/(x1+x2+x3+x4+x5+x6+x7+x8+x9)\} \quad (2)$$

By using equations similar to equation (2) for the remaining ROIs, the control unit 155 can distribute the composition signals acquired in the period T1 and decide the signal components output from the conversion elements 106 of the respective selected ROIs. The control unit 155 acquires the integrated dose of incident radiation by using the sum of the decided signal components and the signals output at the time of measurement of the integrated dose of radiation. As described above, the control unit 155 may control the end of exposure to radiation based on the acquired integrated dose. In addition, upon completion of irradiation with radiation, the control unit 155 causes the readout unit 151 in the period T3 to read out signals for a radiation image which are accumulated in the conversion elements 104 of the pixels 101 based on radiation. The control unit 155 controls the driving circuit 151b to sequentially apply the voltage Von to the signals Vg1 to Vg12 so as to scan the control lines 108, and sequentially transfers the signals accumulated in the conversion elements 104 to the processing circuit 151a via the signal lines 110. At this time, the control unit 155 may control the readout unit 151 so as not to scan a row, of the control lines 108, on which the pixel 101 set as an ROI is located.

In this embodiment, as in the first embodiment described above, the bias power supply 153 and a sensing unit 132 may use different parameters concerning readout operations, such as readout gains. In this case, highly quantitative measurement of the integrated dose of radiation can be implemented by totalizing the signals output from the respective ROIs upon correcting signal components in accordance with differences in parameters.

Output and reset operations for signals from the pixels 101 connected to the control lines 108 (Vg3, Vg6, and Vg9 (Vd1, Vd2, and Vd3)) are intermittently repeated in the period T2. This makes it difficult to use the signals output from the pixels 101 in the period T3 as signals for a radiation image. Accordingly, in generating a radiation image, signals for a radiation image which are output from the pixels 101 connected to the control lines 108 (Vg3, Vg6, and Vg9 (Vd1, Vd2, and Vd3)) may be, for example, interpolated by using the signals output from the neighboring pixels 101. In addition, the conversion elements 104 of the pixels 101, of the pixels 101 connected to the control lines 108 (Vg3, Vg6, and Vg9 (Vd1, Vd2, and Vd3)), which are not designated as ROIs are indispensable for deciding signal components from the conversion elements 104 of the pixels 101 designated as ROIs, as described above. Accordingly, the conversion elements 104 of the pixels 101, of the pixels 101 connected to the control lines 108 (Vg3, Vg6, and Vg9 (Vd1, Vd2, and Vd3)), which are not designated as ROIs can also be regarded as detection units.

In this embodiment, as in the first embodiment, the quantitativity of the integrated dose of radiation incident on detection units (ROIs) of the radiation imaging apparatus 1200 can be improved, and the quality of an obtained radiation image can be improved.

The embodiments of the present invention have been described above. Obviously, however, the present invention is not limited to these embodiments, and the above embodiments can be changed and combined as needed without departing from the spirit of the present invention.

Figure 14:
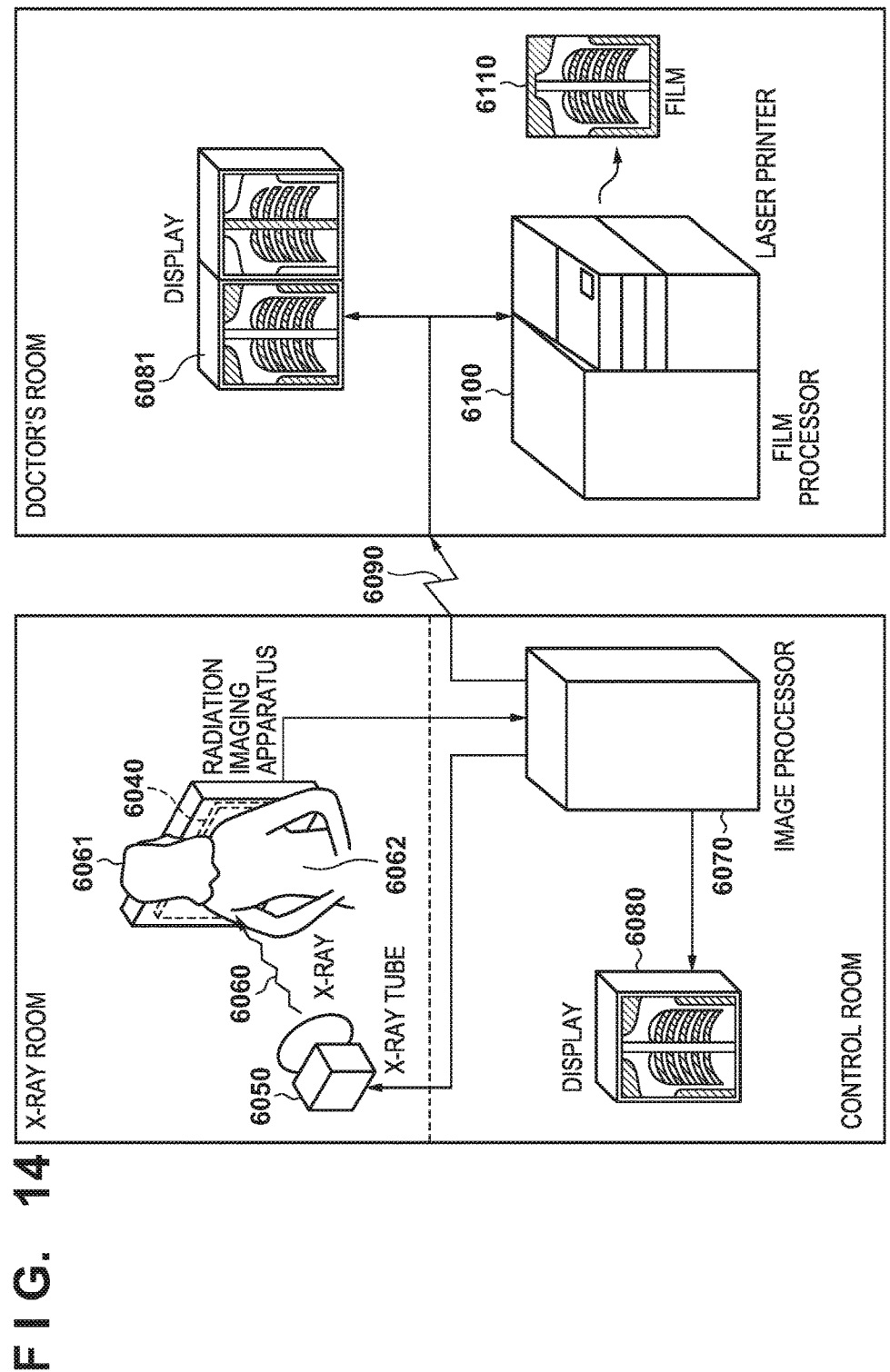
FIG. 14 is a view showing an example of the arrangement of a radiation imaging system using a radiation imaging apparatus according to an embodiment of the present invention.

A radiation imaging system incorporating the radiation imaging apparatuses 200, 700, and 1200 according to the present invention will be exemplarily described below with reference to FIG. 14. An X-ray 6060 generated by an X-ray tube 6050 as a radiation source passes through a chest 6062 of a patient or object 6061, and enters a radiation imaging apparatus 6040 (corresponding to the radiation imaging apparatus 200, 700, or 1200 described above) shown in FIG. 14. The incident X-ray contains internal information of the patient or object 6061. In the radiation imaging apparatus 6040, the scintillator emits light in correspondence with the incidence of the X-ray 6060, and the photoelectric conversion elements photoelectrically convert the light, thereby obtaining electrical information. This information is digitally converted, undergoes image processing by an image processor 6070 serving as a signal processing unit, and can be observed on a display 6080 serving as a display unit in the control room.

This information can be transferred to a remote place by a transmission processing unit such as a network 6090, for example, a telephone, LAN, or Internet. This makes it possible to display the information on a display 6081 serving as a display unit in another place such as a doctor's room, thus allowing a doctor in a remote place to make a diagnosis. In addition, the information can be recorded on a recording medium such as an optical disk. Furthermore, the information can also be recorded on a film 6110 serving as a recording medium by a film processor 6100.

OTHER EMBODIMENTS

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2017-092566, filed May 8, 2017 which is hereby incorporated by reference wherein in its entirety.

What is claimed is:

1. A radiation imaging apparatus comprising an image sensing region including a plurality of conversion elements configured to acquire a radiation image, a plurality of detection units arranged in the image sensing region and configured to monitor incident radiation, a readout unit configured to read out signals from the plurality of detection units, and a control unit, wherein the control unit executes a first operation and a second operation, in the first operation, the control unit causes the readout unit to output a composition signal obtained by composing signals from the plurality of detection units, detects a start of irradiation with radiation based on the composition signal, and shifts to the second operation, and in the second operation, the control unit acquires a plurality of first signals individually read out from the plurality of detection units to the readout unit, decides a signal component, of the composition signal, which is output from a selected detection unit of the plurality of detection units in accordance with a ratio of the first signal from the selected detection unit to a sum of the plurality of first signals, and acquires an integrated dose of radiation incident on the selected detection unit based on the signal component and a first signal, of the plurality of first signals, which is output from the selected detection unit.

2. The apparatus according to claim 1, wherein the control unit acquires the integrated dose based on a sum of the signal component and a first signal, of the plurality of first signals, which is output from the selected detection unit.

3. The apparatus according to claim 1, wherein the control unit causes the readout unit to read out the composition signal with a first gain in the first operation, causes the readout unit to read out the plurality of first signals with a second gain different from the first gain in the second operation, corrects the signal component in accordance with a ratio between the first gain and the second gain, and acquires the integrated dose based on a sum of the corrected signal component and a first signal, of the plurality of first signals, which is output from the selected detection unit.

4. The apparatus according to claim 3, wherein the first gain is lower than the second gain.

5. The apparatus according to claim 1, further comprising a memory unit configured to store the composition signal acquired by the first operation, wherein the control unit decides the signal component by distributing the composition signal stored in the memory unit in accordance with the ratio in the second operation.

6. The apparatus according to claim 1, wherein the control unit determines, based on the integrated dose, whether to stop exposure to radiation, and outputs a signal for stopping irradiation with radiation in accordance with the determination result.

7. The apparatus according to claim 1, wherein the image sensing region includes a plurality of pixels,
each of the plurality of pixels includes any one of the plurality of conversion elements, and
each of some of the plurality of pixels further includes any one of the plurality of detection units.

8. The apparatus according to claim 1, wherein some of the plurality of conversion elements respectively serve as detection units of the plurality of detection units.

9. The apparatus according to claim 1, further comprising a bias power supply configured to supply a common bias voltage to the plurality of detection units and a bias wiring configured to connect the bias power supply to the plurality of detection units,
wherein the control unit acquires the composition signal based on a change in current in the bias wiring in the first operation.

10. The apparatus according to claim 1, wherein the plurality of detection units output signals to the same signal line.

11. The apparatus according to claim 10, further comprising a plurality of detection unit groups each including the plurality of detection units.

12. A radiation imaging system comprising:
a radiation imaging apparatus defined in claim 1; and
a signal processing unit configured to process a signal from the radiation imaging apparatus.

13. A control method for a radiation imaging apparatus comprising an image sensing region including a plurality of conversion elements configured to acquire a radiation image, a plurality of detection units arranged in the image sensing region and configured to monitor incident radiation, and a readout unit configured to read out signals from the plurality of detection units,
the control method including a first step and a second step,
the first step including causing the readout unit to output a composition signal obtained by composing signals from the plurality of detection units, detecting a start of irradiation with radiation based on the composition signal, and shifting to the second step, and
the second step including
acquiring a plurality of first signals individually read out from the plurality of detection units to the readout unit,
deciding a signal component, of the composition signal, which is output from a selected detection unit of the plurality of detection units in accordance with a ratio of the first signal from the selected detection unit to a sum of the plurality of first signals, and
acquiring an integrated dose of radiation incident on the selected detection unit based on the signal component and a first signal, of the plurality of first signals, which is output from the selected detection unit.

14. A non-transitory computer-readable storage medium storing a program for causing a computer to execute a control method for a radiation imaging apparatus comprising an image sensing region including a plurality of conversion elements configured to acquire a radiation image, a plurality of detection units arranged in the image sensing region and configured to monitor incident radiation, and a readout unit configured to read out signals from the plurality of detection units,
the control method including a first step and a second step,
the first step including causing the readout unit to output a composition signal obtained by composing signals from the plurality of detection units, detecting a start of irradiation with radiation based on the composition signal, and shifting to the second step, and
the second step including
acquiring a plurality of first signals individually read out from the plurality of detection units to the readout unit,
deciding a signal component, of the composition signal, which is output from a selected detection unit of the plurality of detection units in accordance with a ratio of the first signal from the selected detection unit to a sum of the plurality of first signals, and
acquiring an integrated dose of radiation incident on the selected detection unit based on the signal component and a first signal, of the plurality of first signals, which is output from the selected detection unit.

* * * * *